(12) United States Patent
Lin et al.

(10) Patent No.: US 11,896,641 B2
(45) Date of Patent: Feb. 13, 2024

(54) PEPTIDE COMPOSITION FROM EARLY HARVESTED RICE AND METHODS FOR SLIMMING OR PROMOTING GROWTH OF PROBIOTICS USING THE SAME

(71) Applicant: TCI CO., LTD., Taipei (TW)

(72) Inventors: Yung-Hsiang Lin, Taipei (TW); Pei-Yi Wu, Taipei (TW)

(73) Assignee: TCI CO., LTD., Taipei (TW)

( * ) Notice: Subject to any disclaimer, the term of this patent is extended or adjusted under 35 U.S.C. 154(b) by 109 days.

(21) Appl. No.: 17/519,583

(22) Filed: Nov. 5, 2021

(65) Prior Publication Data

US 2022/0168377 A1 Jun. 2, 2022

Related U.S. Application Data

(60) Provisional application No. 63/142,497, filed on Jan. 28, 2021, provisional application No. 63/118,748, filed on Nov. 27, 2020.

(30) Foreign Application Priority Data

Sep. 24, 2021 (TW) .................. 110135698

(51) Int. Cl.
  *A61K 36/899* (2006.01)
  *A61K 38/10* (2006.01)
  *A61P 3/10* (2006.01)
  *A61P 3/04* (2006.01)
  *A61K 38/08* (2019.01)

(52) U.S. Cl.
  CPC ............ *A61K 36/899* (2013.01); *A61K 38/08* (2013.01); *A61K 38/10* (2013.01); *A61P 3/04* (2018.01); *A61P 3/10* (2018.01)

(58) Field of Classification Search
  CPC ....... A61K 36/899; A61K 38/08; A61K 38/10
  See application file for complete search history.

(56) References Cited

U.S. PATENT DOCUMENTS

2010/0215782 A1\* 8/2010 Babish .................. A61K 36/00
  514/533

FOREIGN PATENT DOCUMENTS

| CN | 110151796 A | 8/2019 |
| KR | 100773484 B1 | 11/2007 |

OTHER PUBLICATIONS

Role of pigeon pea (*Cajanus cajan* L.) in human nutrition and health: A review, Aruna Talari et al, Asian J. Dairy & Food Res, Agricultural Research Communication Centre, vol. 37 Issue 3, pp. 212-220, 2018.

\* cited by examiner

*Primary Examiner* — Robert A Wax
*Assistant Examiner* — William Craigo
(74) *Attorney, Agent, or Firm* — Chieh-Mei Wang

(57) ABSTRACT

A peptide composition and methods for slimming and/or for promoting the growth of probiotics using early harvested rice prebiotics are provided. The peptide composition or the early harvested rice prebiotics includes at least one peptide as set forth in: SEQ ID NO: 1, SEQ ID NO: 2, SEQ ID NO: 3, SEQ ID NO: 4, SEQ ID NO: 5, SEQ ID NO: 6, SEQ ID NO: 7 and SEQ, ID NO: 8.

10 Claims, 13 Drawing Sheets
Specification includes a Sequence Listing.

PEPTIDE COMPOSITION FROM EARLY HARVESTED RICE AND METHODS FOR SLIMMING OR PROMOTING GROWTH OF PROBIOTICS USING THE SAME

CROSS-REFERENCE TO RELATED APPLICATION

This application claims the benefit of U.S. provisional application Ser. No. 63/118,748, filed on Nov. 27, 2020, U.S. provisional application Ser. No. 63/142,497, filed on Jan. 28, 2021, and claims the priority of Patent Application No. 110135698 filed in Taiwan, on Sep. 24, 2021. The entirety of the above-mentioned patent applications are hereby incorporated by references herein and made a part of the specification.

REFERENCE OF AN ELECTRONIC SEQUENCE LISTING

The contents of the electronic sequence listing (P211607USI_ST25.txt, Size: 1.8 KB; and Date of Creation: Nov. 5, 2021) is herein incorporated by reference in its entirety.

BACKGROUND

Technical Field

The present invention relates to use of early harvested rice, and particularly to use of early harvested rice for preparing a composition for slimming and a composition for promoting the growth of probiotics.

Related Art

*Oryza sativa* is commonly known as rice. Rice is a one- to two-year-old herbaceous plant of the genus *Oryza*, and the most important kind of food in the genus *Oryza*. It is also known as Asian cultivated rice and Asian rice. It is monocotyledonous, and the plant grows upright in clusters.

A complete seed of rice is called paddy, which is 0.5 to 0.7 cm long and in the shape of an ellipse or long ellipse. After the husk is removed by the rice hulling machine, brown rice can be obtained. After the brown rice is processed and milled to remove the bran layer, germ and a small part of the endosperm, white rice for consumption is obtained. White rice is the staple food of human beings. It can also be brewed into rice wine or sake or processed into foods such as rice noodles, rice bran, and radish cakes.

Prebiotics are compounds in food that induce the growth or activity of beneficial microorganisms such as bacteria and fungi. Prebiotics refer to substances that are not easily broken down by the upper digestive tract in the body, but are more easily used by microorganisms when they come to the intestine. Prebiotics provide a better source of nutrients for probiotics, so as to promote the proliferation of good bacteria and reduction of bad bacteria.

SUMMARY

In view of this, the present invention provides use of early harvested rice prebiotics for preparing a composition for slimming and a composition for promoting the growth of probiotics. In addition to providing a nutrient source for probiotics, the early harvested rice prebiotics provided, by the present invention is also rich in nutrients required by the human body, and can further improve the body's health.

In an embodiment, the early harvested rice prebiotics include at least one peptide as set forth in: SEQ ID NO: 1, SEQ NO: 2, SEQ ID NO: 3, SEQ ID NO: 4, SEQ ID NO: 5, SEQ ID NO: 6, SEQ ID NO: 7 and SEQ ID NO: 8.

In an embodiment, the early harvested rice prebiotics are prepared from early harvested rice. The early harvested rice are rice seeds that are harvested within 15 to 25 days after flowering. In an embodiment, the early harvested rice prebiotics include dietary fiber.

In an embodiment, the early harvested rice prebiotics are prepared from the early harvested rice by aqueous extraction and hydrolysis with a complex enzyme.

In an embodiment, the early harvested rice prebiotics are used to increase the content of leptin, adiponectin or glucose transporter type 4 (GLUT4) protein.

In an embodiment, the early harvested rice prebiotics are used to increase the amounts of probiotics in the human intestinal tract. In an embodiment, the probiotics are *Lactobacillus acidophilus, Lactobacillus reuteri, Lactobacillus rhamnosus, Lactobacillus paracasei* or *Rhizopus bifidus*.

In an embodiment, the early harvested rice prebiotics are used to reduce the body fat content. In an embodiment, the early harvested rice prebiotics are used to reduce the waist circumference, trunk fat content and leg fat content of the human body. In an embodiment, the early harvested rice prebiotics are used to reduce fasting blood glucose, fasting insulin or insulin resistance.

In an embodiment, the composition is a food, drink or nutritional supplement. In an embodiment, an effective dose of the early harvested rice prebiotics in the composition is 500 mg.

The present invention provides a peptide composition, which includes the peptide composition includes: at least one peptide as set forth in: SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 8; or a peptide as set forth in SEQ ID NO: 9. In an embodiment, the peptide composition is prepared from early harvested rice. The early harvested rice are rice seeds that are harvested within 15 to 25 days after flowering.

To sum up, the early harvested rice prebiotics according to any embodiment is used for preparing a composition for slimming and a composition for promoting the growth of probiotics. In addition, the early harvested, rice prebiotics include at least one peptide as set forth in SEQ ID NO: 1 to SEQ ID NO: 8. In some embodiments, the early harvested rice prebiotics are used to increase the content of leptin, adiponectin or glucose transporter type 4 (GLUT4) protein. In an embodiment, the early harvested rice prebiotics are used to increase the number of probiotics in the human intestinal tract. In an embodiment, the early harvested rice prebiotics are used to reduce the body fat content. In an embodiment, the early harvested rice prebiotics are used to reduce the waist circumference, trunk fat content and leg fat content of the human body. In an embodiment, the early harvested rice prebiotics are used to reduce fasting, blood glucose, fasting insulin or insulin resistance.

BRIEF DESCRIPTION OF THE DRAWINGS

FIG. 10 is a graph showing the results of changes in insulin resistance in a human subject experiment.

DETAILED DESCRIPTION

Figure 1:
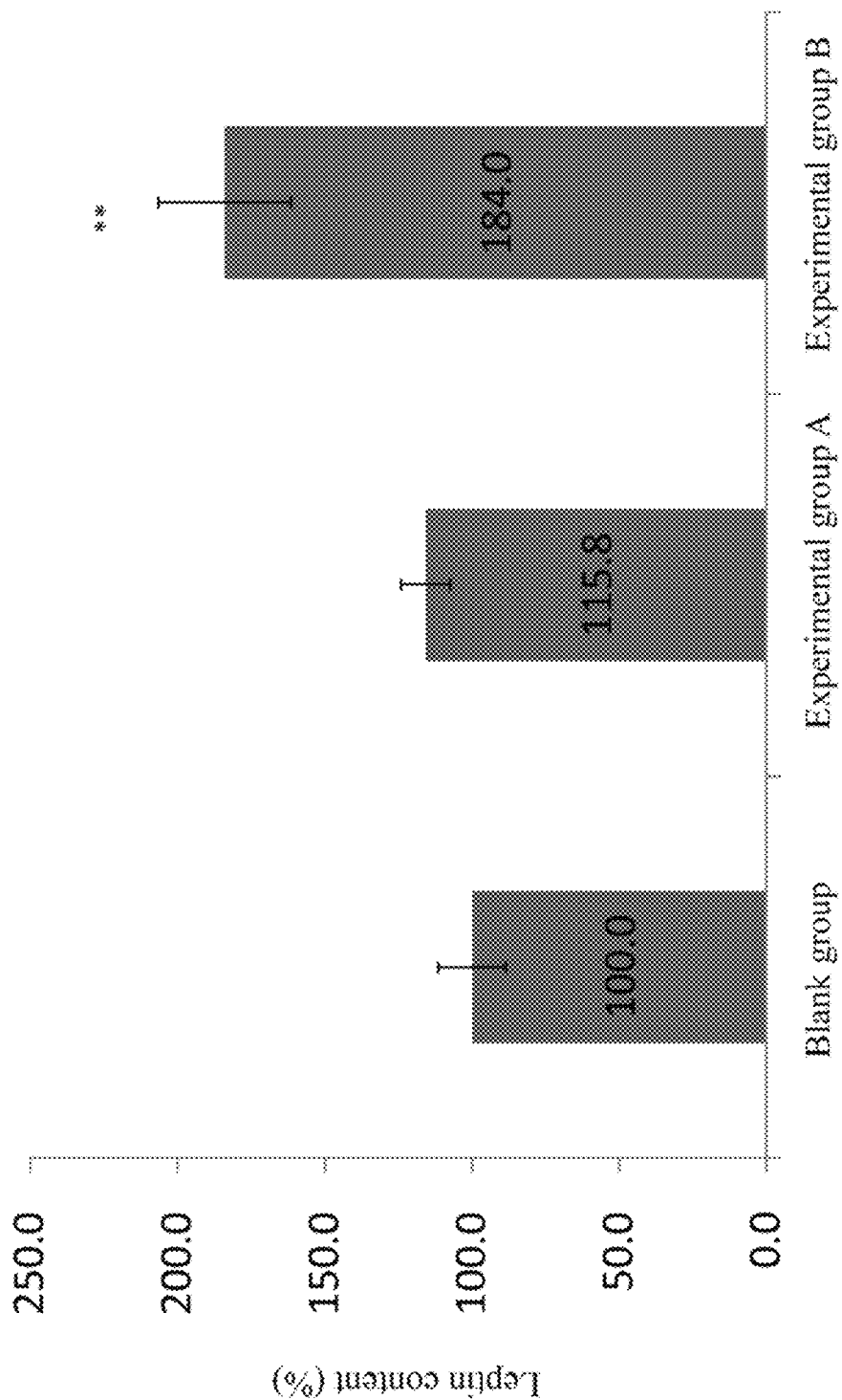
FIG. 1 is a diagram showing the result of increasing the content of leptin by early harvested rice prebiotics according to an embodiment of the present invention.

In some embodiments, the early harvested rice prebiotics can be used for preparing a composition for slimming. In some embodiments, the early harvested rice prebiotics can be used for preparing a composition for promoting the growth of probiotics. The early harvested rice prebiotics include at least one amino acid sequence as set forth in: SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8, and each amino acid sequence is a peptide fragment prepared from early harvested rice through a specific enzyme hydrolysis and a specific extraction process.

It should be understood that "peptides" are substances between amino acids and proteins, and are composed of multiple amino acids. In addition, the peptide as a biologically active substance can be an "isolated peptide" or a "synthetic peptide". The "isolated peptide" refers to a peptide fragment isolated from an organism or a derivative of an organism, and the peptide fragment has biological activity. The "synthetic peptide" refers to a peptide fragment synthesized according to the desired amino acid sequence by means of instruments or manual experimental operations, and this peptide fragment has biological activity. In addition, the term "isolated peptide" mentioned herein is equivalent to "peptide isolated" or "peptide obtained through isolation", and the term "synthetic peptide" is equivalent to "synthesized peptide" or "peptide obtained through synthesis".

Herein, when the peptide includes multiple amino acid sequences as set forth in SEQ ID NO: 1 to SEQ ID NO: 8, these amino acid sequences may be peptide fragments isolated from the same protein or peptide fragments isolated from different proteins.

In some embodiments, the peptide fragments can be derived from energy storage proteins, for example, glutelin or its fragments, Glutelin7.8/31K or its fragments, prolamin (Os05g0329400 protein) or its fragments, etc.

In some embodiments, the peptide fragments can be derived from glycosyl transfer proteins, for example, glycosyltransferase or its fragments, glucose-1-phosphate adenylyltransferase, etc. The glycosyl transfer proteins can inhibit the differentiation of adipocytes to reduce achieve the accumulation of lipids. The lack of glycosyl transfer proteins will reduce insulin secretion.

In some embodiments, the peptide fragment can be derived from Alpha-1,4 glucan phosphorylase. In some embodiments, the peptide fragment can be derived from superoxide dismutase. In some embodiments, the peptide fragment can be derived from aldehyde dehydrogenase. In some embodiments, the peptide fragment can be derived from nudix hydrolase domain-containing protein, glyco_hydro_18 domain-containing protein or uncharacterized protein. Superoxide dismutase can reduce oxidative stress, inhibit obesity caused by a high-fat diet, and reduce visceral fat content.

In some embodiments, the early harvested rice refers to immature seeds of rice (*Oryza sativa*). In some embodiments, the early harvested rice refers to immature seeds of rice that have not undergone any processing. In some embodiments, the early harvested rice is seeds that are harvested in the maturity stage (also known as the dough stage), i.e., within 15 to 25 days after flowering, and is also called green rice because of its blue outer shell. In some embodiments, the early harvested rice is intact seeds that are harvested in 15th to 25th days of the flowering period. The intact seeds refer to seeds that have not been dehulled, i.e., the intact seed includes rice husk, rice bran, rice germ and endosperm. In some embodiments, rice varieties can be endemic to Taiwan, for example, Tainan 11 and Kaohsiung 147.

In some embodiments, the early harvested rice prebiotics refer to early harvested rice powder. In some embodiments, the early harvested rice prebiotics refer to a powder that is obtained by drying and grinding the early harvested rice. In some embodiments, the early harvested rice prebiotics refer to a powder that is obtained by drying and grinding the early harvested rice followed by sieving with a 120-mesh sieve.

In some embodiments, the early harvested rice prebiotics are prepared from the early harvested rice by a hydrolysis step, a deactivation step and a sterilization step. For example, the early harvested rice prebiotics are prepared by chopping the early harvested rice, mixing the chopped early harvested rice with water and alkaline protease for hydrolysis, then heating to 85° C. to 95° C. and holding for 10 to 30 minutes for deactivation, and heating to 135° C., to 140° C. and holding for 3 seconds to 5 seconds for sterilization.

In some embodiments, the hydrolysis includes adding alkaline protease and an appropriate amount of water to the early harvested rice prebiotics, so that the alkaline protease can act for a period of time under a proper environment. In some embodiments, the proper environment refers to a temperature of 40° C.-60° C., and the period of time refers to 1-5 hours. In some embodiments, the deactivation step refers to heating the early harvested rice prebiotics that have undergone the hydrolysis step to deactivate it. For example, the heating can refer to reacting at 85° C. to 95° C. for 10 to 30 minutes. In some embodiments, alkaline protease (Alcalase 2.4FG, Novozyme) is used in the hydrolysis step.

In some embodiments, after the deactivation step, a filtration step and a sterilization step can also be included to improve the preservation quality of the product. For example, after the deactivation step, after being cooled, the early harvested rice is clarified by filtering with a filter paper, and then the filtered early harvested rice is subjected to ultra-high temperature (UHT) sterilization. Ultra-high temperature sterilization refers to holding at 135° C. to 140° C. for 3 seconds to 5 seconds. Finally, a 0.2 µm filter membrane can be used to filter off bacteria and remove fine impurities.

In an embodiment, the early harvested rice prebiotics further include dietary fiber.

In an embodiment, the early harvested rice prebiotics are used to increase the content of leptin. Leptin can suppress appetite and increase metabolism, to increase energy consumption in the body. In an embodiment, the early harvested rice prebiotics are used to increase the content of adiponectin. Adiponectin is a functional peptide secreted by adipocytes, and is related to the maintenance of the metabolic balance of glucose and lipids in the body. The increase in the adiponectin content can reduce accumulation of lipids and promote muscle cells to burn fat into energy and prevent coronary artery diseases. In an embodiment, the early harvested rice prebiotics are used to increase the content of glucose transporter 4 (GLUT4). GLUT4 is a member of a family of integral membrane glucose transporters. The increase in the GLUT4 content can promote the absorption of glucose in the blood by muscle, fat and liver tissues, and bring glucose into the cells of the above-mentioned tissues, providing a function of balancing blood glucose.

In an embodiment, the early harvested rice prebiotics are used to increase the number of probiotics in the human intestinal tract. In an embodiment, the probiotics are *Lactobacillus acidophilus, Lactobacillus reuteri, Lactobacillus rhamnosus, Lactobacillus paracasei* or *Rhizopus bifidus.*

In an embodiment, the early harvested rice prebiotics are used to reduce the body fat content. In an embodiment, the early harvested rice prebiotics are used to reduce the waist circumference, trunk fat content and leg fat content of the human body. In an embodiment, the early harvested rice prebiotics are used to reduce fasting blood glucose, fasting insulin or insulin resistance.

In an embodiment, the composition is a food, drink or nutritional supplement. In an embodiment, an effective dose of the early harvested rice prebiotics in the composition is 500 mg.

In some embodiments, any of the compositions mentioned above can be an edible product (i.e., food composition). In other words, the edible product contains a specific content of the early harvested rice prebiotics. In some embodiments, the edible product can be an ordinary food, a food for special health use (FoSHU), a dietary supplement or a food additive.

The FoSHU, or referred to as a functional food, refers to a food that is processed to not only supply nutrients but also provide desirable bioregulatory function. The term "functional" refers to providing nutrients for the structure and functional regulation of the human body or providing a desirable effect for health care purposes such as physiological effects. The food of the present invention can be prepared by a method commonly used in the art, and in the above preparation, it can be prepared by adding raw materials and ingredients commonly added in the art. In addition, the dosage form of the food can be prepared without limitation as long as it is regarded as a dosage form of a food. The food composition of the present invention can be prepared in a variety of dosage forms. Different from ordinary drugs, the food composition using food as a raw material has no side effects that may occur due to long-term drug use, and is easy to carry. Therefore, the food of the present invention can be taken as an auxiliary agent for enhancing the immune enhancement effect.

In some embodiments, the edible product can be prepared into a dosage form suitable for oral administration by using techniques well known to those skilled in the art. In some embodiments, ordinary foods can be but not limited to: beverages, fermented foods, bakery products or seasonings.

The composition may further include a physiologically acceptable carrier. The type of carrier is not particularly limited, and any carrier commonly used in the art may be used.

In addition, the composition may contain additional ingredients that are commonly used in food compositions to improve smell, taste, aesthetics, and the like. For example, the composition may contain 0.1-5 wt % of vitamins A, C, D, F, B1, B2, B6, B12, niacin, biotin, folate, panthotenic acid, etc. In addition, the composition may contain minerals such as zinc (Zn), iron (Fe), calcium (Ca), chromium (Cr), magnesium (Mg), manganese (Mn), copper (Cu), chromium (Cr), etc. In addition, the composition may contain amino acids such as lysine, tryptophan, cysteine, and valine.

In addition, the composition may contain food additives such as oxidation inhibitors (e.g., butylhydroxyanisole (BHA) and butylhydroxytoluene (BHT)), colorants (e.g., coal tar dye), fragrances (e.g., vanillin, lactones), color couplers (e.g., sodium nitrite and sodium nitrite), preservatives (e.g., potassium sorbate, sodium benzoate, salicylic acid, and sodium dehydroacetate), bleaching agent (e.g., sodium sulfite), seasonings (e.g., MSG sodium glutamate), sweeteners (e.g., dulcin, cyclamate, saccharin, and sodium), bulking agents (e.g., alum, and D-potassium hydrogen tartrate), fortifiers, emulsifiers, thickeners (paste), filming agents, glue bases, foam inhibitors, solvents, improvers, etc. One or more of the above-mentioned additives can be selected and added in an appropriate amount according to the type of food.

In some embodiments, the early harvested rice prebiotics of any embodiment can be added (as a food additive) during the preparation of raw materials or added (as a food additive) during the food production process by a conventional method, so as to be formulated with any edible material into an edible product for humans and non-human animals.

In some embodiments, the composition may be a medicine. In other words, the medicine contains an effective content of the early harvested rice prebiotics.

In some embodiments, the medicine can be prepared into a dosage form suitable for intestinal or oral administration by using techniques well known to those skilled in the art. These dosage forms include, but are not limited to: tablet, troche, lozenge, pill, capsule, dispersible powder or granule, solution, suspension, emulsion, syrup, elixir, slurry and the like.

In some embodiments, the medicine can be prepared into a dosage form suitable for parenteral or topical administration by using techniques well known to those skilled in the art. These dosage forms include, but are not limited to: injection, sterile powder, external preparation and the like. In some embodiments, the medicine can be administered by a parenteral route selected from the group consisting of: subcutaneous injection, intraepidermal injection, intradermal injection and intralesional injection.

In some embodiments, the medicine may further contain a pharmaceutically acceptable carrier that is widely used in drug preparation technologies. For example, the pharmaceutically acceptable carrier may include one or more of the following agents: solvent, buffer, emulsifier, suspending agent, decomposer, disintegrating agent, disintegrating agent, dispersing agent, binding agent, excipient, stabilizing agent, chelating agent, diluent, gelling agent, preservative, wetting agent, lubricant, absorption delaying agent, liposome and the like. The selection and quantity of these reagents fall within the scope of professionalism and routine techniques of those skilled in the art.

In some embodiments, the pharmaceutically acceptable carrier contains a solvent selected from the group consisting of: water, normal saline, phosphate buffered saline (PBS), and aqueous solution containing alcohol.

Example 1: Preparation of Early Harvested Rice Prebiotics

Raw Materials:

(1) intact seeds of Tainan 11 rice variety harvested within 15 to 25 days after flowering were used as early harvested rice.

(2) Alkaline protease (Alcalase 2.4FG, Novozyme) (commercially available).

First, the dried early harvested rice is crushed to powder. The early harvested rice powder is early harvested rice prebiotics A.

Next, the early harvested rice prebiotics A was mixed in reverse osmosis (RO) filtered water at 1:20 (w/v) to form an early harvested rice solution.

The early harvested rice prebiotics A was enzymatically hydrolyzed by adding, alkaline protease to the early harvested rice solution at a ratio of 1:100 (W/W), to form a hydrolyzed early harvested rice solution. The hydrolysis time was 4 hours, the hydrolysis temperature was 55° C., and the pH value of the early harvested rice solution was 6.

The hydrolyzed early harvested rice solution was heated to 85° C. and held for 30 minutes to deactivate the alkaline protease. After being cooled, the hydrolyzed early harvested rice solution was filtered with No. 1 filler paper (Advantec). The hydrolyzed early harvested rice solution was sterilized after the filtration. Herein, sterilization refers to holding at 135° C. for 4 seconds. Finally, a 0.2 μm filter membrane can be used to filter off bacteria and remove fine impurities. The final product is the early harvested rice prebiotics B.

Example 2: Component Identification

The components of the early harvested rice prebiotics A of Example 1 and other candidate early harvested rice as well as commercially available brown rice and white rice were identified. This component identification was carried out by SGS Taiwan Ltd.

Sample 1 was the early harvested rice prebiotics A prepared from early harvested rice of Tainan 11 in Example 1 of the present invention. Sample 2 was prepared by using early harvested rice of Tainan 14 as the raw material according to the process steps of the early harvested rice prebiotics A in Example 1 of the present invention. Sample 3 was prepared by using early harvested rice of Kaohsiung 147 as the raw material according to the process steps of the early harvested rice prebiotics A in Example 1 of the present invention. Sample 4 was prepared by using commercially available unhusked mature brown rice (Tainan 11) as the raw material according to the process steps of the early harvested rice prebiotics A in Example 1 of the present invention. Sample 5 was prepared by using commercially available dehulled mature white rice (Tainan 11) as the raw material according to the process steps of the early harvested rice prebiotics A in Example 1 of the present invention. 100 g of each sample was weighed, and the contents of calories, carbohydrates, dietary fiber, crude protein, crude fat, calcium, magnesium, iron, sodium and potassium in the samples were identified respectively. The result is shown in Table 1 below.

TABLE 1

| | Sample 1 | Sample 2 | Sample 3 | Sample 4 | Sample 5 |
|---|---|---|---|---|---|
| Calories (kcal) | 330.7 | 373.6 | 348.3 | 371.2 | 353 |
| Carbohydrate (g) | 65.5 | 74.7 | 71.5 | 76.9 | 78 |
| Dietary fiber (g) | 4.8 | 6 | 5.1 | 3.4 | 0.5 |
| Crude protein (g) | 9.3 | 8.1 | 6.3 | 7.9 | 6.9 |
| Crude fat (g) | 2.1 | 3.1 | 2.17 | 2.4 | 0.6 |
| Calcium (mg) | 12.5 | 19.2 | 19.7 | 12.7 | 10 |
| Magnesium (mg) | 138.2 | 152.8 | 143.8 | 135.9 | 12 |
| Iron (mg) | 1.03 | 1.53 | 1.47 | 0.97 | 0.2 |
| Sodium (mg) | 0.57 | 2.17 | 1.72 | 1.07 | 1 |
| Potassium (mg) | 298.7 | 262.5 | 352.9 | 170.9 | 76 |

As can be seen from the above-mentioned composition identification, samples 1 to 3 belonging to the early harvested rice have lower total calories than white rice or brown rice, lower carbohydrate content than white rice or brown rice, higher dietary fiber content which is up to 12 times that of white rice, and higher amounts of magnesium, iron, and potassium in trace elements than those of white rice or brown rice. The crude protein contents of sample 1 and sample 2 are also higher than those of other samples.

In general, from the perspective of modern nutrition, the early harvested rice is more in line with the nutritional needs of modern people. In particular, sample 1 has the lowest calories, carbohydrate and sodium contents, and contains the highest crude protein content.

Example 3: Total Polysaccharide Identification

The total polysaccharides of the early harvested rice prebiotics A in Example 1 and early harvested rice of other varieties were identified. Polysaccharides are important biopolymers, which can store energy (such as starch) and form the structure (such as chitin) in organisms.

Sample 1 was the early harvested rice prebiotics A prepared from early harvested rice of Tainan 11. Sample 2 was prepared by using early harvested rice of Tainan 14 as the raw material according to the process steps of the early harvested rice prebiotics A in Example 1 of the present invention. Sample 3 was prepared by using early harvested rice of Kaohsiung 147 as the raw material according to the process steps of the early harvested rice prebiotics A in Example 1 of the present invention.

Herein, the total polysaccharide content was determined by a phenol-sulfuric acid method 100 μL of each of samples 1, 2, and 3 was mixed with glucose standard solutions of different concentrations (0, 25, 50, 75, 100, and 125 mg mL) in test tubes respectively. Then 0.5 mL of phenol solution and 2.5 mL of sulfuric acid were added for reaction. A spectrophotometer was used to measure the absorbance value of the test tube at 750 nm, and the absorbance value was converted into the percentage of water-soluble polysaccharide content.

The analysis results showed that the total polysaccharide content of sample 1 was 1.29%, the total polysaccharide content of sample 2 was 3.37%, and the total polysaccharide content of sample 3 was 1.74%.

Example 4: Total Polyphenol Identification

The components of the early harvested rice prebiotics A of Example 1 and other candidate early harvested rice as well as commercially available brown rice and white rice were identified. Polyphenols are a group of phytochemicals, and usually have a strong antioxidant effect.

Sample 1 was the early harvested rice prebiotics A prepared from early harvested rice of Tainan 11. Sample 2 was prepared by using early harvested rice of Tainan 14 as the raw material according to the process steps of the early harvested rice prebiotics A in Example 1 of the present invention. Sample 3 was prepared by using early harvested rice of Kaohsiung 147 as the raw material according to the process steps of the early harvested rice prebiotics A in Example 1 of the present invention. Sample 4 was prepared by using commercially available dehulled mature white rice as the raw material according to the process steps of the early harvested rice prebiotics A in Example 1 of the present invention.

Each sample was diluted 10 times with water and then 100 mL of the dilution was transferred into a centrifuge tube. Then, 500 μL of Folin-Ciocalteu phenol reagent was added to the centrifuge tube, mixed with the diluted sample and allowed to stand for 3 minutes. Then 400 μL, of 7.5% sodium carbonate was added to and evenly mixed with the mixture, and allowed to stand for 30 minutes to obtain a reaction solution to be tested. After the second standing, 200 μL of the reaction solution to be tested was taken into a 96-well plate, and the absorbance of the reaction solution to be tested was measured at 750 nm.

In addition, a standard curve was prepared using gallic acid as a standard. Herein, 0 μL/mL, 20 μL/mL, 40 μL/mL, 60 μL/mL, 80 μL/mL, and 100 μL/mL gallic acid standard solutions were prepared, and 100 μL of each concentration standard solution was taken into a 10 mL centrifuge tube respectively. 500 μL of Folin-Ciocalteu phenol reagent was added to the centrifuge tube and mixed with the standard solution, allowed to stand for 3 minutes; then 400 μL of 7.5% sodium carbonate was added to and evenly mixed with the mixture, and allowed to stand for 30 minutes to obtain a standard reaction solution. 200 μL of the standard reaction solution was taken in a 96-well plate and the absorbance of the standard reaction solution was measured at 750 nm to obtain a standard curve.

Then, the absorbance of the reaction solution to be tested was converted into the total polyphenol content per 100 g of the sample by using the standard curve. Herein, the total polyphenol content of sample 1 was 79.6 mg, the total polyphenol content of sample 2 was 86.5 mg, the total polyphenol content of sample 3 was 93.2 mg, and the total polyphenol content of sample 4 was only 1.5 mg.

Example 5: Peptide Sequencing and Protein Identification

Peptide sequencing and protein identification of the early harvested rice prebiotics B in Example 1 were carried out. At the same time, a brown rice prebiotic was prepared from commercially available brown rice (i.e., mature and unhulled rice) by the same process steps as that of the early harvested rice prebiotics B in Example 1. Peptide sequencing and protein identification were then performed on the early harvested rice prebiotics B and the brown rice prebiotic to further understand the differences between the two.

First, the early harvested rice prebiotics B was diluted with deionized water to a concentration of 20 mg/ml, and then protein identification was carried out by liquid chromatography mass spectrometry (LC-MS/MS). In addition, the liquid chromatography mass spectrometer (LC-MS/MS) is a quadrupole time-of-flight tandem mass spectrometer system (Q-TOF). The model of the liquid chromatography system (LC system) is UltiMate 3000 RSLCnano LC Systems (from Thermo Fisher Scientific), and the model of the mass spectrometer is Exactive™ Plus Orbitrap Mass Spectrometer. Herein, the separation column number installed in the liquid chromatography system is C18 separation column (Acclaim PepMap C18, 75 μm I.D.×25 cm nanoViper. 2 μm, 100 Å (Thermo Fisher Scientific)). The solution system used by the liquid chromatography mass spectrometer is buffer solution A (0.1% Formic acid dissolved in 100% deionized water) and buffer solution B (0.1% Formic acid dissolved in 100% ACN). The separation gradient set by the liquid chromatography mass spectrometer is from 5% buffer solution B to 90% buffer solution B, the flow rate is set to 300 nl/min and the gradient elution is carried out for 30 minutes.

In the settings of the mass spectrometer, the survey scan is set to scan all ionized separated peptides in the range of 100 m/z (mass-to-charge ratio) to 1500 m/z. In the information dependent aqcuisition (CID) mode, the detection range for peptides is set to be 100-5000 daltons (Da). Then, these separated peptides were analyzed to generate multiple MS/MS maps correspondingly, and these MS/MS maps were searched in databases (NCBI and UniProt) by using the Mascot analysis program, to obtain amino acid sequences of the peptides unique to the early harvested rice prebiotics B compared with the brown rice prebiotic, as shown in Table 2.

TABLE 2

| Sequence number | Sequence | Molecular weight |
| --- | --- | --- |
| SEQ ID NO: 1 | RQGDVIALPAGVA | 1.27 kDa |
| SEQ ID NO: 2 | ILAGDHL | 0.74 kDa |
| SEQ ID NO: 3 | NSIDSSTIASNIK | 1.35 kDa |
| SEQ ID NO: 4 | VSDSQIPLTGAHSIIGR | 1.75 kDa |
| SEQ ID NO: 5 | ISPSAPVVR | 0.93 kDa |
| SEQ ID NO: 6 | VSPDVQF | 0.79 kDa |
| SEQ ID NO: 7 | VRSLPNYGGL | 1.08 kDa |

TABLE 2-continued

| Sequence number | Sequence | Molecular weight |
|---|---|---|
| SEQ ID NO: 8 | PHYSNGATL | 0.96 kDa |
| SEQ ID NO: 9 | VRQQYGIAASPF | 1.34 kDa |

As can be seen from Table 2 above, the SEQ ID NO: 9 peptide fragment belonging to prolamin (obtained by genome editing from Os05g0329400) is an internal control peptide, and its presence in both the early harvested rice prebiotics B and the brown rice prebiotic can be detected by sequencing.

There are eight kinds of peptides that can only be seen in the early harvested rice prebiotics B, namely, the peptides as set forth in SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO; 8.

Identification information about functional proteins to which the above-mentioned peptides belong is shown in Table 3 below.

TABLE 3

| Sequence number | Identification information |
|---|---|
| SEQ ID NO: 1 | Glutelin 17.8/31K |
| SEQ ID NO: 2 | Glucose-1-phosphate adenylyltransferase |
| SEQ ID NO: 3 | Alpha-1,4 glucan phosphorylase |
| SEQ ID NO: 4 | Superoxide dismutase |
| SEQ ID NO: 5 | Aldehyde dehydrogenase |
| SEQ ID NO: 6 | Nudix hydrolase domain-containing protein |
| SEQ ID NO: 7 | Glyco_hydro_18 domain-containing protein |
| SEQ ID NO: 8 | Improtin N-terminal domain-containing protein |
| SEQ ID NO: 9 | Gliadin (Os05g0329400 protein) |

That is, SEQ ID NO: 1 belongs to a peptide fragment of Glutelin I, SEQ ID NO: 2 belongs to a peptide fragment of glucose-1-phosphate adenylyltransferase, and SEQ ID NO: 3 belongs to a peptide fragment of alpha-1,4 glucan phosphorylase, SEQ ID NO: 4 belongs to a peptide fragment of superoxide dismutase, SEQ ID NO: 5 belongs to a peptide fragment of aldehyde dehydrogenase, SEQ ID NO: 6 belongs to a peptide fragment of nudix hydrolase domain-containing protein, SEQ ID NO: 7 belongs to a peptide fragment of glyco_hydro_18 domain-containing protein, SEQ ID NO: 8 belongs to a peptide fragment of improtin N-terminal domain-containing protein, and SEQ ID NO: 9 belongs to a peptide fragment of gliadin.

Therefore, it can be seen that the early harvested rice prebiotics B contain the amino acid sequences of the nine peptides isolated above, namely, SEQ ID NO: 1 to SEQ ID NO: 9. It can be reasonably inferred that the early harvested rice prebiotics B have the functional proteins corresponding to the above-mentioned peptides, and should have the functions of the functional proteins. In addition, because the early harvested rice prebiotics B is prepared from the early harvested rice prebiotics A, it means that the early harvested rice prebiotics A also contains the amino acid sequences of the nine peptides mentioned above.

Example 6: Evaluation of the Effect of Increasing the Leptin Content

First, mouse adipocytes 3T3-L1. (purchased from ATCC® CL-173™) were cultured in a pre-adipocyte expansion medium, which contained 90% Dulbecco's Modified Eagle's Medium (DIEM) (Gibco), 10% bovine serum (purchased from Gibco, USA), and to which 1% of penicillin-streptomycin (purchased from Gibco, USA) was added.

Next, 200 μL of the pre-adipocyte expansion medium was added to each well of a 96-well culture plate, so that each well had 1×10$^4$ 3T3-L1 cells. After culturing at 37° C. for 48 hours, the pre-adipocyte expansion medium was removed.

Then, a differentiation medium was added, which contained 90% Dubek's modified Eagle's medium, 10% fetal bovine serum (FBS), 1% penicillin-streptomycin, 1.0 μM/mL dexamethasone (DEXA, brand Sigma), 0.5 mM/mL, methylisobutylxanthine (IBMX, brand Sigma) and 1.0 μg/mL insulin (Sigma), and was replaced with fresh differentiation medium every 2 days. After 4 days, the differentiation medium was replaced with an adipocyte maintenance medium, which contained 90% Dubek's Modified Eagle's Medium (DMEM) (Gibco), 10% Fetal Bovine Serum (FBS), 1% penicillin-streptomycin and 1.0 μg/mL insulin, and was replaced with fresh adipocyte maintenance medium every 2 days. After 7-10 days since the start of differentiation induction, the cells had fully differentiated. Next, the formation of lipid droplets was observed using a microscope.

Then, the above-mentioned differentiated 3T3-L1 cells were divided into three groups, including experimental group A, experimental group B and blank group. 0.06.25% of the early harvested rice prebiotics B were added to the cells of experimental group A, 0.125% of the early harvested rice prebiotics B were added to the cells of experimental group B, while the cells in the blank group were not treated.

After culturing for 12 days (where the adipocyte maintenance medium was replaced with fresh adipocyte maintenance medium every 48 hours), the medium was collected and the Leptin content of each group was obtained using Mouse LEP (Leptin) ELISA Kit (Elabscience).

FIG. 1 is a diagram showing the result of increasing the content of leptin by the early harvested rice prebiotics according to an embodiment of the present invention. It can be seen from FIG. 1 that compared with the blank group, the leptin content of experimental group A increased (by 15.79%), and the leptin content of experimental group B increased significantly (by 83.99%). The results of this example show that the early harvested rice prebiotics of the present invention can effectively increase the leptin content, thereby achieving the effect of regulating body weight or slimming.

Example 7: Evaluation of the Effect of Increasing the Adiponectin Content

First, mouse bone marrow stromal cells (hereinafter referred to as OP9 cells) were cultured in a medium, which contained a MEMAM cell culture medium (Minimum Essential Medium Alpha Medium, purchased from Gibco, USA) and 20% fetal bovine serum (Fetal Bovine Serum, purchased from Gibco, USA, Cat #10437-028), and to which 0.1% penicillin-streptomycin (purchased from Gibco, USA) was added. Herein, the OP9 cells were the OP9 cell line (ATCC CRL-2749) purchased from the American Type Culture Collection (ATCC®).

Then, 8×10$^4$ OP9 cells and 500 μL of the above-mentioned medium were inoculated in each well of a 24-well culture plate, and cultured at 37° C. for 7 days. During this 7-day cell culture period, the medium was changed every 3 days. After 7 days, the formation of lipid droplets in the cells was observed with a microscope (400× magnification) to confirm that the cells had fully differentiated into adipocytes.

Then, the differentiated adipocytes were divided into the following three groups: experimental group A, experimental group B and blank group. 0.0625% of the early harvested rice prebiotics B were added to the cells of experimental group A, 0.125% of the early harvested rice prebiotics B were added to the cells of experimental group B, while the cells in the blank group were not treated.

After incubating at 37° C. for 24 hours, the culture medium in the well was transferred to a 1.5 ml microcentrifuge tube. After centrifugation at 1000×g for 15 minutes at 2-8° C., the supernatant was transferred to a new 1.5 ml microcentrifuge tube, diluted by 2000 times, and then tested using an adiponectin detection reagent kit (purchased from CUSABIO, model CSB-E07272m). The detailed operation steps can be performed by referring to the instruction manual attached to the adiponectin detection reagent kit, which can be found at https://www.cusabio.com/uploadfile/Ins/CSB-E07272m.pdf.

Finally, the OD reading of each group at 548 nm was read with an ELISA reader (BioTek) (the larger the O.D. value, the higher the content of adiponectin). Finally, student t-test in Excel software was used for statistical analysis. Through comparison and conversion of the absorbance and multiplication by the dilution factor, the converted adiponectin contents of experimental group A and experimental group B when the adiponectin content of the blank group was 100% were as shown in FIG. 2.

Figure 2:
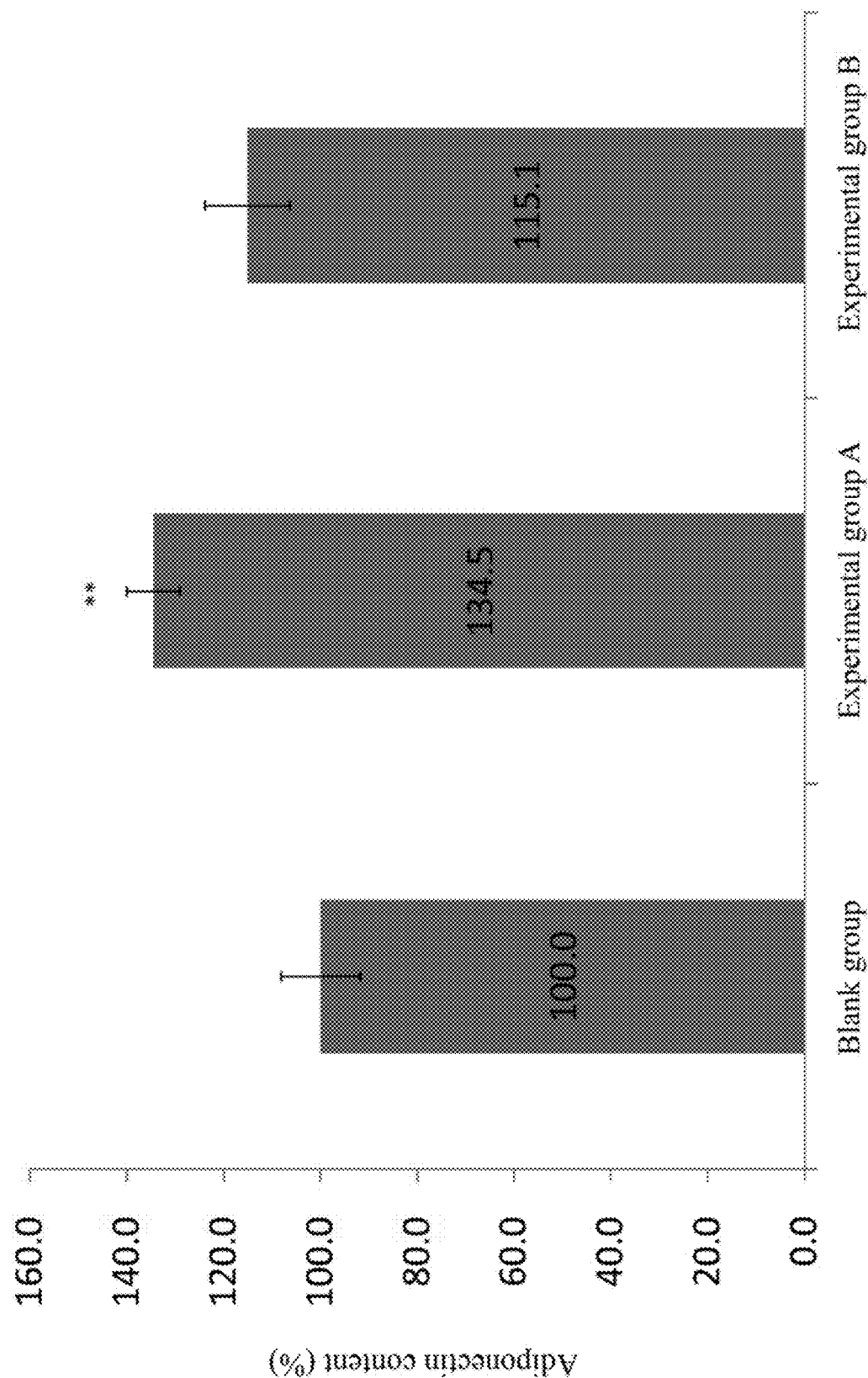
FIG. 2 is a diagram showing the result of increasing the content of adiponectin by early harvested rice prebiotics according to an embodiment of the present invention.

FIG. 2 is a diagram showing the result of increasing the content of adiponectin by the early harvested rice prebiotics according to an embodiment of the present invention. It can be seen from FIG. 2 that compared with the blank group, the adiponectin content of experimental group A increased significantly (by 34.5%), and the adiponectin content of experimental group B increased (by 15.1%). The results of this example show that the early harvested rice prebiotics of the present invention can effectively increase the adiponectin content and have the potential to reduce fat.

Example 8: Evaluation of the Effect of Improving the Expression Level of Glucose Transporter 4 (GLUT4)

First, liver tissue cells (hereafter referred to as HepG2 cells) were cultured in a medium, which contained Dulbecco's modified Eagle cell culture medium and 10% fetal bovine serum (purchased from Gibco, USA), and to which 1% penicillin-streptomycin (purchased from Gibco, USA) was added. Herein, the HepG2 cells were the HepG2 cell line (ATCC® HB-8065™) purchased from the American Type Culture Collection (ATCC®).

Next, 1×10$^5$ HepG2 cells and 2 mL of the above medium were inoculated in each well of a 6-well culture plate, and cultured at 37' C for 72 hours.

Then, the HepG2 cells were divided into the following three groups: experimental group A, experimental group B and blank group. 0.0625% of the early harvested rice prebiotics B were added to the cells of experimental group A, 0.125% of the early harvested rice prebiotics B were added to the cells of experimental group B, while the cells in the blank group were not treated.

After incubating at 37° C. for 24 hours, 0.5M insulin (purchased from Sigma, model 19278-5ML) was added for 24 hours. After washing twice with 1 mL of 1×PBS (purchased from Gibco, USA), 200 µL of trypsin was added to each well, and allowed to react for 5 minutes in the dark. The cells were put in a test tube containing a medium, centrifuged at 300 g for 5 minutes to remove the suspension, washed again with 1×PBS, centrifuged again at 300 g for 5 minutes to remove the supernatant, resuspended with 2% FBS for 30-60 minutes, centrifuged again at 300 g for 5 minutes to remove the supernatant, and then washed with 1×PBS to pellet the cells. Finally, the GLUT4 antibody (purchased from Invitrogen, model MA5-17176) was added at a ratio of 1:200, and after 30 minutes, washed twice with 1×PBS; Alexa 488 goat IgG (purchased from invitrogen, model A11001) was added at a ratio of 1:200, and after 10 minutes, washed twice with 1×PBS.

Finally, the fluorescence intensity of each group was read using a flow cytometer (model BD Accuri C6 Plus). Through comparison and conversion, when the expression level of GLUT4 in the blank group is 100%, the expression levels of GLUT4 in experimental group A and experimental group B are shown in FIG. 3.

Figure 3:
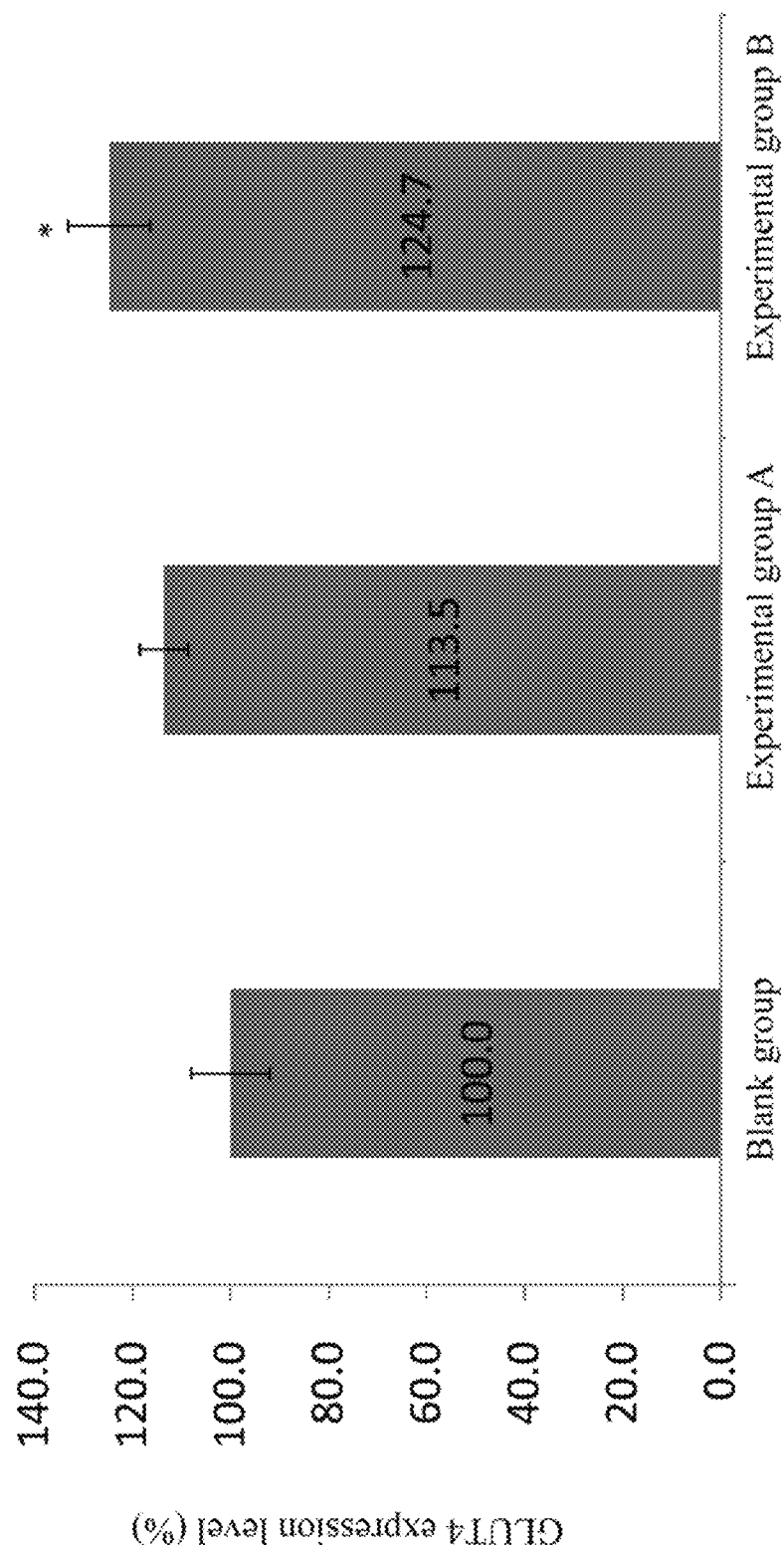
FIG. 3 is a diagram showing the result of improving the expression level of glucose transporter 4 (GLUT4) by early harvested rice prebiotics according to an embodiment of the present invention.

FIG. 3 is a diagram showing the result of improving the expression level of GLUT4 by the early harvested rice prebiotics according to an embodiment of the present invention. It can be seen from FIG. 3 that compared with the blank group, the expression level of GLUT4 in experimental group A increased (by 13.5%), and the expression level of GLUT4 in experimental group B increased significantly (by 24.7%). The results of this example show that the early harvested rice prebiotics of the present invention can regulate the utilization rate of glucose and have the potential to lose weight.

Example 9: Evaluation of the Effects of Different Raw Materials in Promoting the Growth of Probiotics In order to evaluate the effects of different raw materials in promoting the growth of probiotics, in this evaluation, based on the fact that the rate of growth of probiotics promoted by fructooligosaccharides is 100%, the relative growth rate of probiotics in each experimental group was calculated.

The sources of raw materials used in each experimental group were as follows:

(1) Blank group: Fructooligosaccharides, purchased from MEIJI CO., Ltd.

(2) Experimental group: Early harvested rice prebiotics A prepared in Example 1.

(3) Control group a: Cactus, prepared according to the process steps of the early harvested rice prebiotics A in Example 1 of the present invention.

(4) Control group b: Burdock, prepared according to the process steps of the early harvested rice prebiotics A in Example 1 of the present invention.

(5) Control group c: Bamboo shoot husk, prepared according to the process steps of the early harvested rice prebiotics A in Example 1 of the present invention.

(6) Control group d: Mung bean husk, prepared according to the process steps of the early harvested rice prebiotics A in Example 1 of the present invention In this evaluation, *Bacillus coagulans* TCI711 strain, *Lactobacillus salivarius* TCI153 strain, and *Streptococcus thermophilus* TCI633 strain were used for subsequent evaluation.

The *Bacillus coagulans* TCI711 strain was deposited at the Food Industry Research and Development Institute (FIRDI) in Taiwan (with a deposit number of BCRC 910807 and DSM33163). The TCI711 strain has the effects of reducing the concentration of heavy metals in the blood, reducing the damage of oxidative substances to liver cells, enhancing the activity of liver cell mitochondria, and reducing the formation of fatty liver.

The *Lactobacillus salivarius* TCI153 strain was deposited at the FIRDI (with a deposit number of BCRC 910982 and DSM33503). The TCI153 strain has the effects of improving skin, promoting cell reconstruction, accumulating collagen, and promoting cell synthesis of elastin.

The *Streptococcus thermophilus* TCI633 strain was deposited in the FIRDI (with a deposit number of BCRC 910636). The TCI633 strain has the effects of heating osteoporosis, reducing bone loss, increasing bone density, and strengthening bones.

The pre-cultured TCI711 strain TCI153 strain and TCI633 strain were respectively added into a medium (volume 5 ml) containing 1% (w/w) of each raw material at the inoculum of 3% (about 1×104 CFU/mL), and cultured at 37° C. for 48 hours. After culturing, the cell count was counted by a dilution spreading method.

Figure 4:
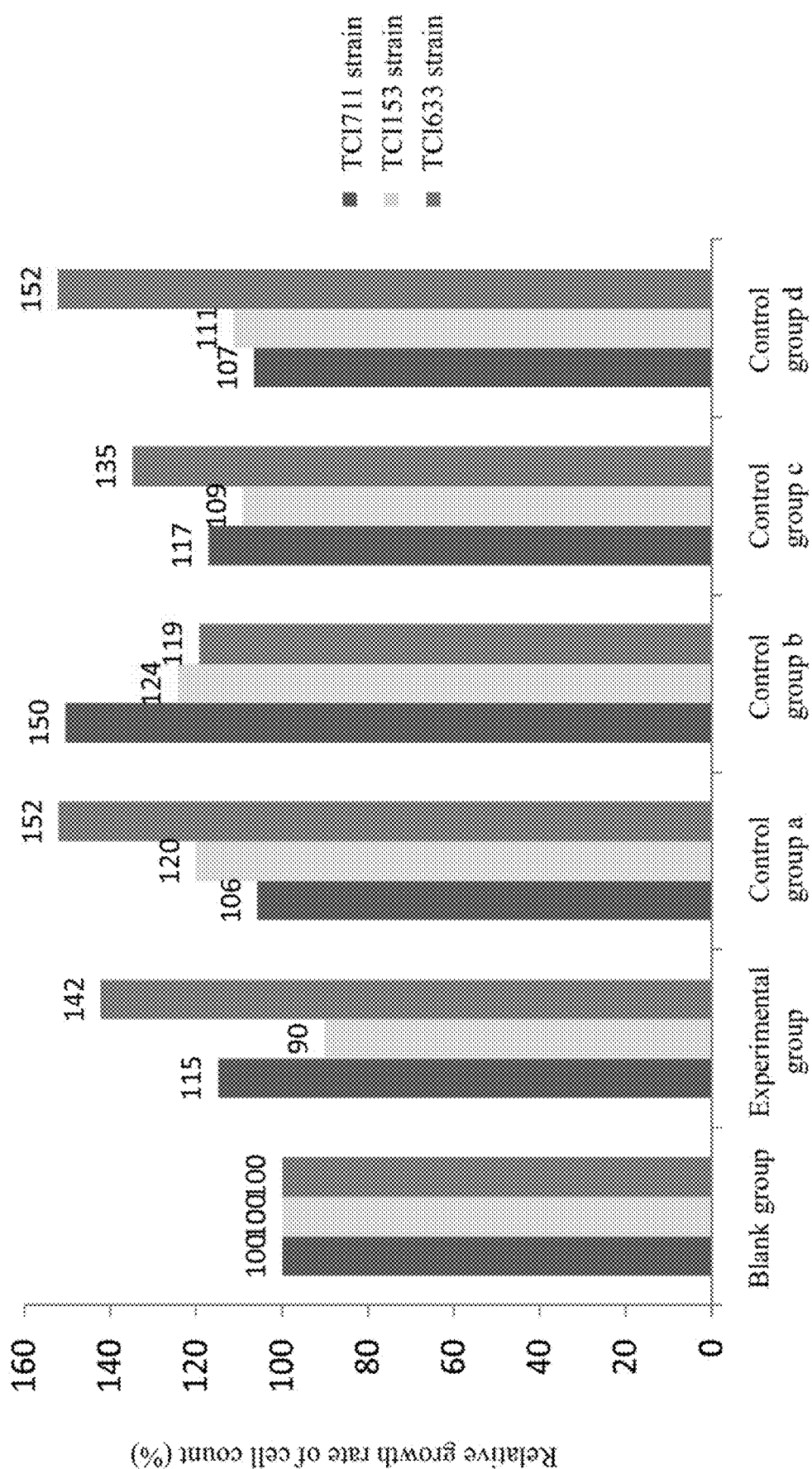
FIG. 4 is a graph showing the evaluation results of the effects of different plant materials in promoting the growth of probiotics.

FIG. 4 is a graph showing the evaluation results of the effects of different raw materials in promoting the growth of probiotics. It can be seen from FIG. 4 that compared with the blank group, the early harvested rice prebiotics A of the experimental group had a better growth-promoting effect on *Bacillus coagulans* than fructooligosaccharides (an increase of 15%), the early harvested rice prebiotics A of the experimental group had a better growth-promoting effect on *Streptococcus thermophilus* than fructooligosaccharides (an increase of 42%), and the early harvested rice prebiotics A in the experimental group did not have a better growth-promoting effect on *Lactobacillus salivarius* than fructooligosaccharides, but could still reach 90% of its effect.

The results of this example show that the early harvested rice prebiotics of the present invention can effectively promote the growth of different kinds of probiotics, especially for *Bacillus coagulans* and *Streptococcus thermophilus*.

Example 10: Evaluation of the Effect of Promoting the Growth of Probiotics

The purpose is to evaluate the effects of the early harvested rice prebiotics in promoting the growth of different kinds of probiotics. The types of probiotics evaluated included: *Lactobacillus acidophilus, Lactobacillus reuteri, Lactobacillus rhamnosus, Lactobacillus paracasei* and *Rhizopus bifidus*.

The probiotic strains used in each experimental group were as follows:

(1) Blank group A: Fructooligosaccharides+*Lactobacillus acidophilus*.

(2) Experimental group A: Early harvested rice prebiotics A prepared in Example 1+*Lactobacillus acidophilus*.

(3) Blank group B: Fructooligosaccharides+*Lactobacillus rhamnosus*.

(4) Experimental group B: Early harvested rice prebiotics A prepared in Example 1+*Lactobacillus rhamnosus*.

(5) Blank group C: Fructooligosaccharides+*Lactobacillus paracasei*.

(6) Experimental group C: Early harvested rice prebiotics A prepared in Example 1+*Lactobacillus paracsei*.

(7) Blank group D: Fructooligosaccharide+*Lactobacillus reuteri*.

(8) Experimental group D: Early harvested rice prebiotics A prepared in Example 1+*Lactobacillus reuteri*.

(9) Blank group E: Fructose oligosaccharide+*Rhizopus bifidus*.

(10) Experimental group E: Early harvested prebiotics A prepared in Example 1+*Rhizopus bifidus*.

In this evaluation, *Lactobacillus acidophilus* was purchased from the American Type Culture Collection (ATCC) (ATCC 4356), *Lactobacillus reuteri* was purchased from the ATCC (ATCC PTA-6475), TCI366 *Lactobacillus rhamnosus* was purchased from the FIRDI (with a deposit number of BCRC910942 and DSM33290), TCI058 *Lactobacillus paracasei* was purchased from the FIRDI (with a deposit number of BCRC910882 and DSM33286), or *Rhizobium bifidus* was purchased from the ATCC (with a deposit number of ATCC BAA-999).

The above-mentioned *Lactobacillus acidophilus* strain, *Lactobacillus reuteri, Lactobacillus rhaninosus, Lactobacillus paracasei,* or *Rhizobium bifidus* strain activated by pre-culture was added into a medium (volume 5 ml) containing 1% (w/w) fructooligosaccharide or early harvested rice prebiotics A at the inoculum of 3% (about 1×10$^4$ CFU/mL), and cultured at 37° C. for 48 hours. Then the OD value was measured using a spectrophotometer. That is, the turbidity of the medium was measured and then converted into the relative cell count. The wavelength of 600 nm was used to measure the concentration of viable bacteria in each group.

Figure 5:
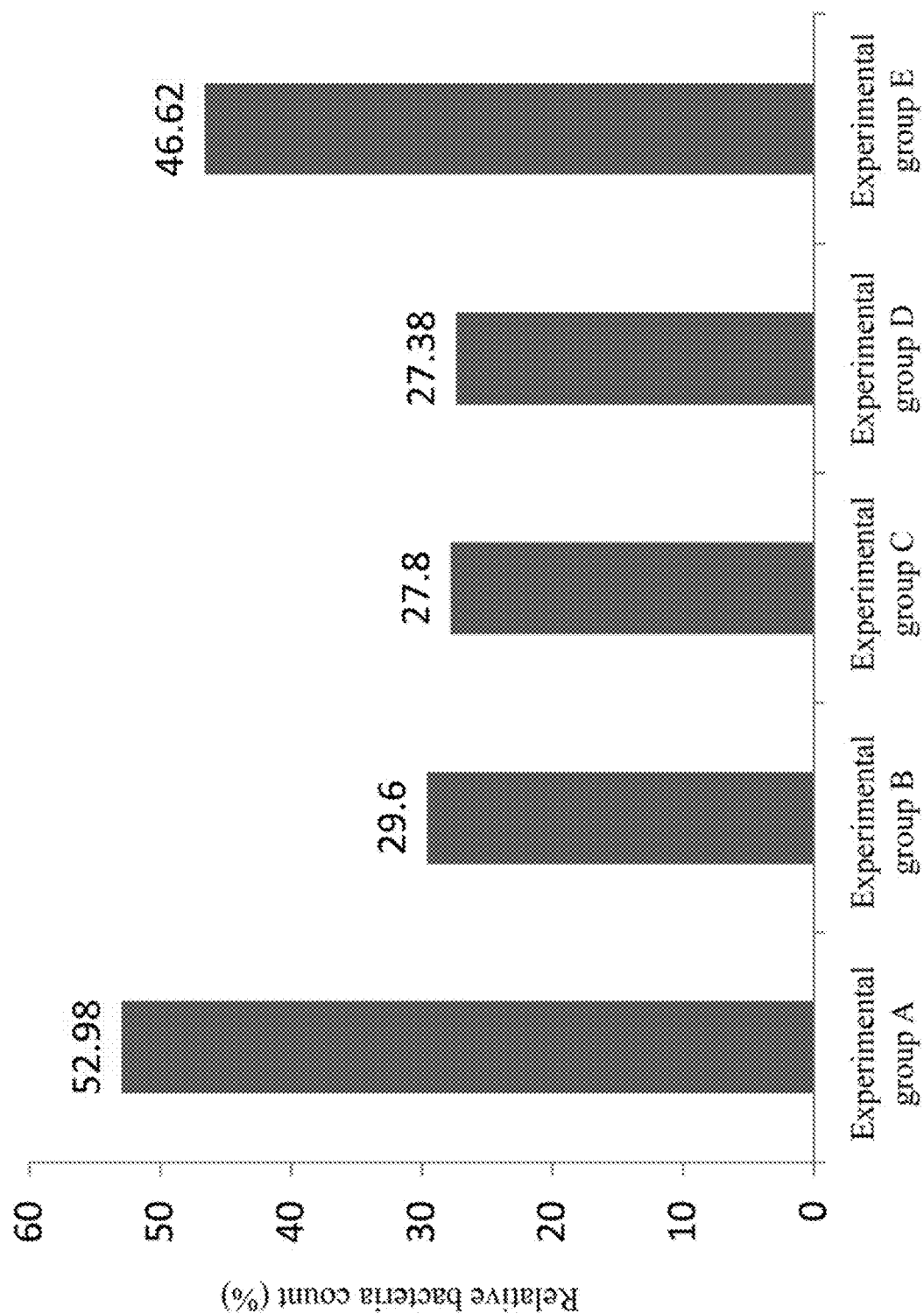
FIG. 5 is a graph showing the evaluation results of the effects of early harvested rice prebiotics in promoting the growth of probiotics according to an embodiment of the present invention.

FIG. 5 is a graph showing the evaluation results of the effects of an early harvested rice prebiotics in promoting the growth of probiotics according to an embodiment of the present invention. In this evaluation, based on the fact that the rate of growth of probiotics promoted by fructooligosaccharides in each blank group was 1%, the growth rate of probiotics in each experimental group was expressed by a relative cell count. For example, based on the fact that the rate of growth of probiotics promoted by fructooligosaccharides in blank group A was 1%, the growth rate of probiotics in each experimental group expressed by the relative cell count was 52.98%. Since the data of each blank group in FIG. 5 was all 1, the data of each blank group was not plotted in FIG. 5 for brevity and ease of reading of FIG. 5.

It can be seen from FIG. 5 that the early harvested rice prebiotics in experimental group A had a significantly better growth-promoting effect on *Lactobacillus acidophilus* than fructooligosaccharides (with an increase of 52.98%), the early harvested rice prebiotics in experimental group B had a significantly better growth-promoting effect on *Lactobacillus reuteri* than fructooligosaccharides (with an increase of 29.6%), the early harvested rice prebiotics in experimental group C had a significantly better growth-promoting effect on *Lactobacillus paracasei* than fructooligosaccharides (with an increase of 27.8%), the early harvested rice prebiotics in experimental group D had a significantly better growth-promoting effect on *Lactobacillus reuteri* than fructooligosaccharides (with an increase of 27.38%), and the early harvested rice prebiotics in experimental group E had a better growth-promoting effect on *Rhizobium bifidus* than fructooligosaccharides (with an increase of 46.62%).

The results of this example show that the early harvested rice prebiotics of the present invention can effectively promote the growth of different species of probiotics, especially for *Lactobacillus acidophilus* and *Rhizopus bifidus*.

Example 11: Evaluation of Early Harvested Rice Through Human Subject Experiment

There were 8 subjects in total, and the selected subjects were between 24 and 40 years old. 4 subjects were grouped into experimental group A, and the other 4 subjects were grouped into experimental group B.

The subjects in experimental group A directly took steamed early harvested rice having the peptides as set forth in SEQ ID NO: 1 to SEQ ID NO: 8, and each subject took 180 g per day, as a supplement to the normal daily diet. After 1 week, the changes in body weight, total body fat, trunk body fat, waist circumference and hip circumference were measured.

The subjects in experimental group B directly took steamed white rice, and each subject took 180 g per day. After 1 week, the changes in body weight, total body fat, trunk body fat, waist circumference and hip circumference were measured.

Herein, the change refers to the difference obtained by subtracting the result value of an item after 1 week from the initial value of the item before the start of the test.

Figure 6:
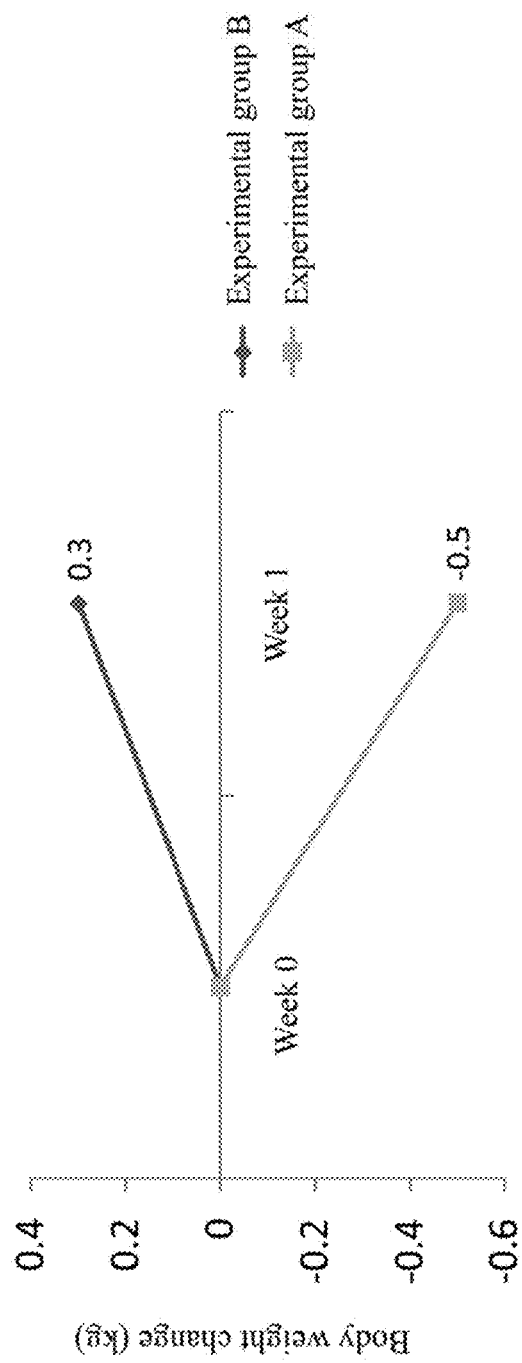
FIG. 6 is a graph showing the result of body weight changes as evaluated in a human subject experiment for the slimming effect.

FIG. 6 is a graph showing the result of body weight changes as evaluated in a human subject experiment for the slimming effect. The average weight of the four subjects in experimental group A decreased by 0.5 kg, and the average weight of the four subjects in experimental group B increased by 0.3 kg.

Figure 7:
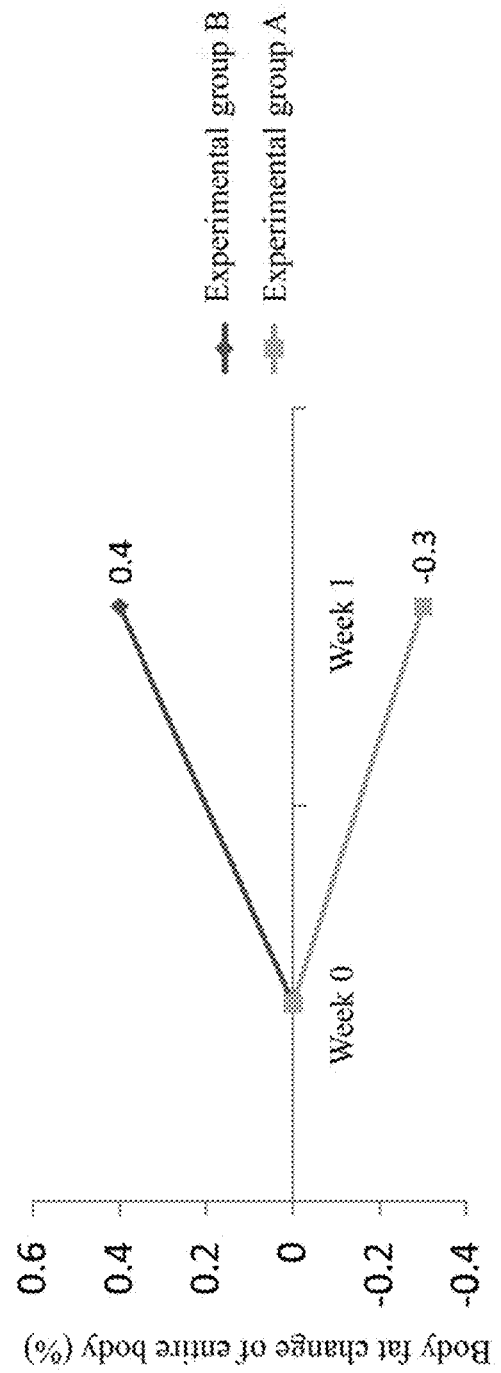
FIG. 7 is a graph showing the result of body fat changes of the entire body as evaluated in a human subject experiment for the slimming effect.

FIG. 7 is a graph showing the result of body fat changes of the entire body as evaluated in a human subject experiment for the slimming effect. The average total body fat of the four subjects in experimental group A decreased by 0.3%, and the average total body fat of the four subjects in experimental group B increased by 0.4%.

Figure 8:
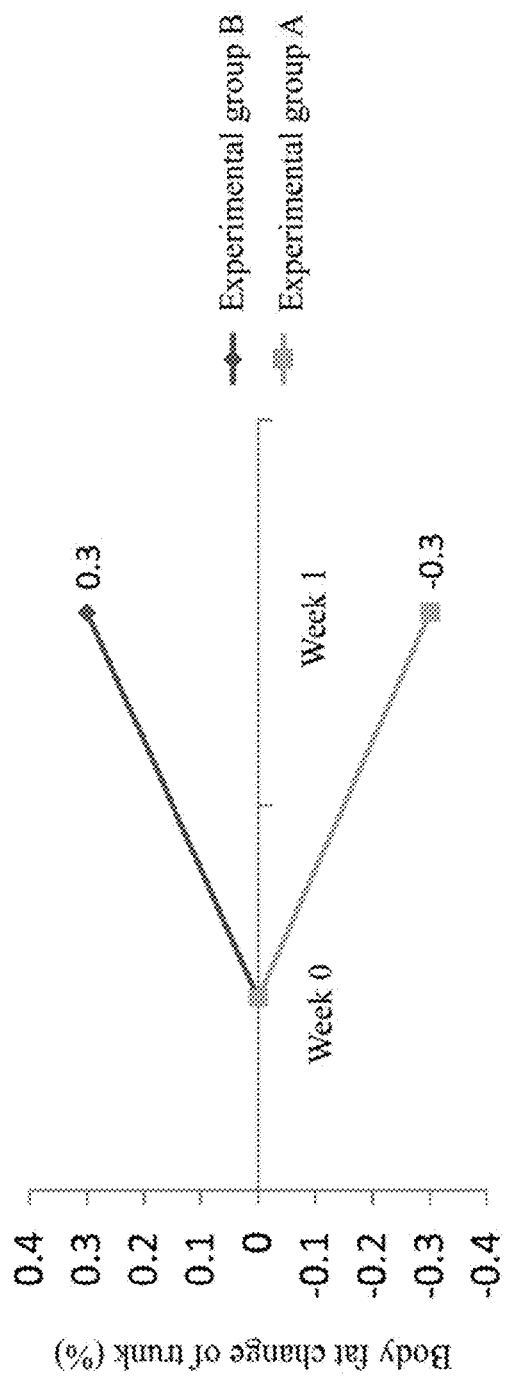
FIG. 8 is a graph showing the result of body fat changes of the trunk as evaluated in a human subject experiment for the slimming effect.

FIG. 8 is a graph showing the result of body fat changes of the trunk as evaluated in a human subject experiment for the slimming effect. The average trunk body fat of the four subjects in experimental group A decreased by 0.3%, and the average trunk body fat of the four subjects m experimental group B increased by 0.3%.

Figure 9:
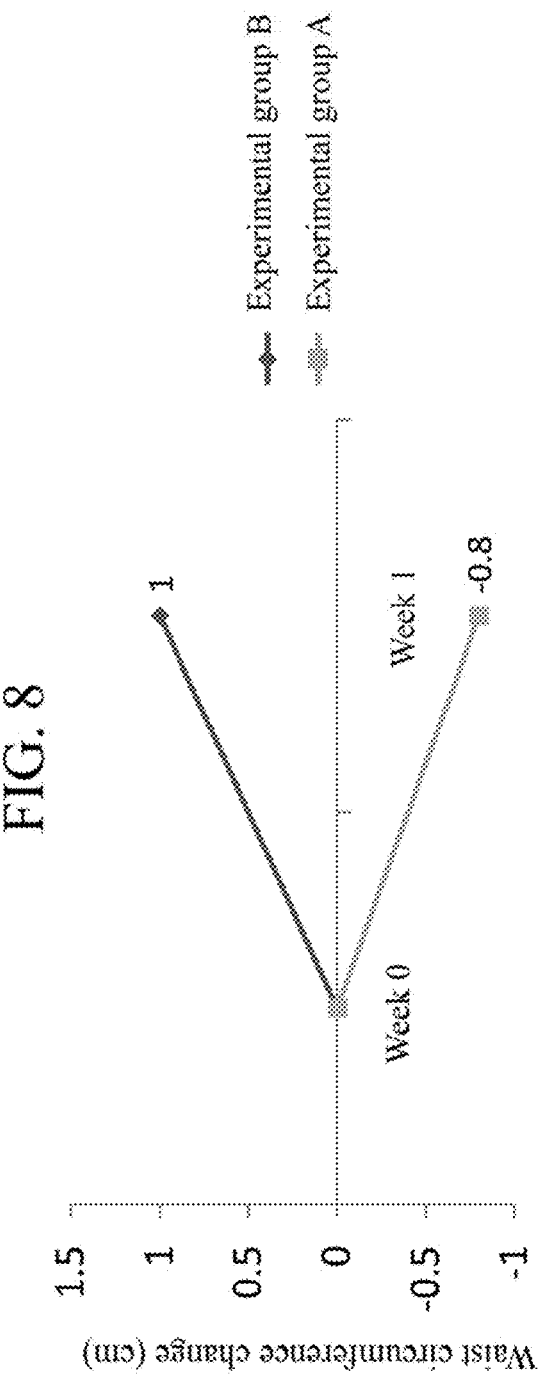
FIG. 9 is a graph showing the results of waist circumference changes as evaluated in a human subject experiment for the slimming effect.

FIG. 9 is a graph showing the results of waist circumference changes as evaluated in a human subject experiment for the slimming effect. The average waist circumference of the four subjects in experimental group A decreased by 0.8 cm, and the average waist circumference of the four subjects in experimental group B increased by 1 cm.

Figure 10:
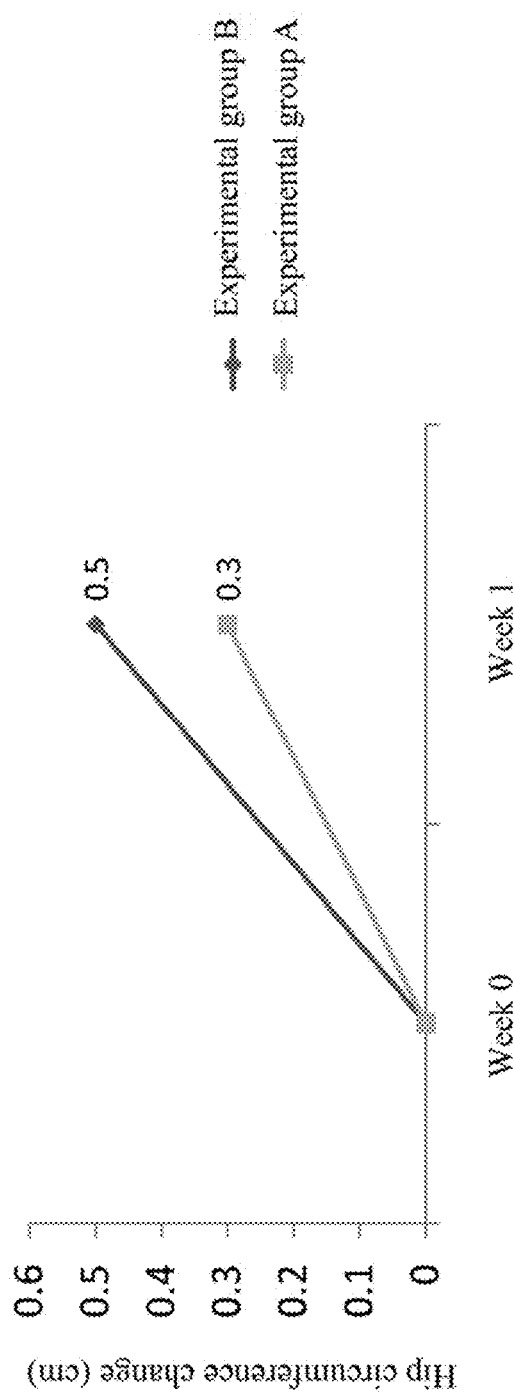
FIG. 10 is a graph showing the results of hip circumference changes as evaluated in a human subject experiment for the slimming effect.

FIG. 10 is a graph showing the results of hip circumference changes as evaluated in a human subject experiment for the slimming effect. The average waist circumference of the four subjects in experimental group A increased by 0.3 cm, and the average waist circumference of the four subjects in experimental group B increased by 0.5 cm.

Example 12. Evaluation of Early Harvested Rice Prebiotics Through Human Subject Experiment The subjects took the early harvested rice prebiotics A prepared in Example 1. Each subject took 500 mg per day. After four weeks, changes in items such as total body fat, trunk body fat, waist circumference, total fat mass and percentage, trunk fat content, leg fat mass, fasting blood glucose, fasting insulin and insulin resistance were measured. Herein, there were 10 subjects, and all the selected subjects had a body fat content greater than 25%.

Figure 11:
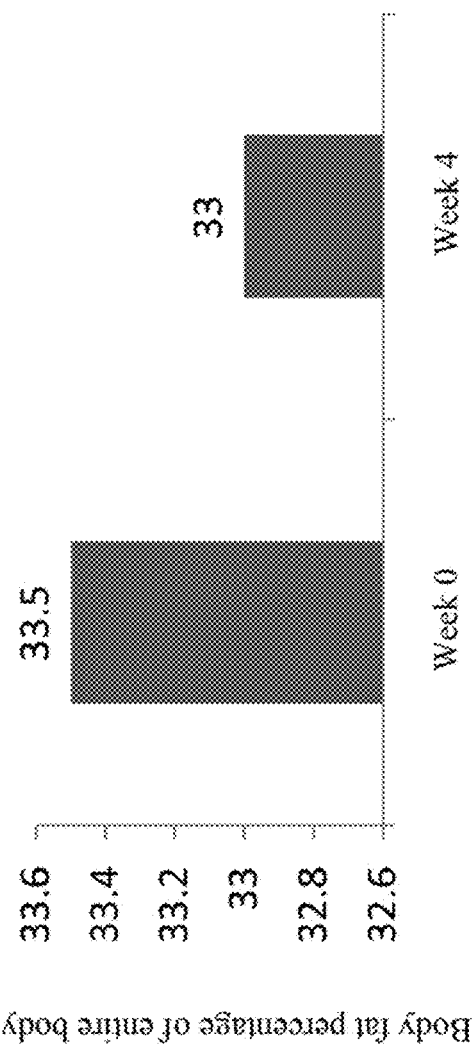
FIG. 11 is a graph showing the results of changes in body fat content of the entire body as evaluated in a human subject experiment.

FIG. 11 is a graph showing the results of changes in body fat content of the entire body as evaluated in a human subject experiment. The initial average body fit content of the 10 subjects was 33.5%, and the final average body fat content of the 10 subjects was 33.0% after taking the early harvested rice prebiotics for four weeks. This means that taking the early harvested rice prebiotics for four weeks can reduce the body fat content by 0.5%.

Figure 12:
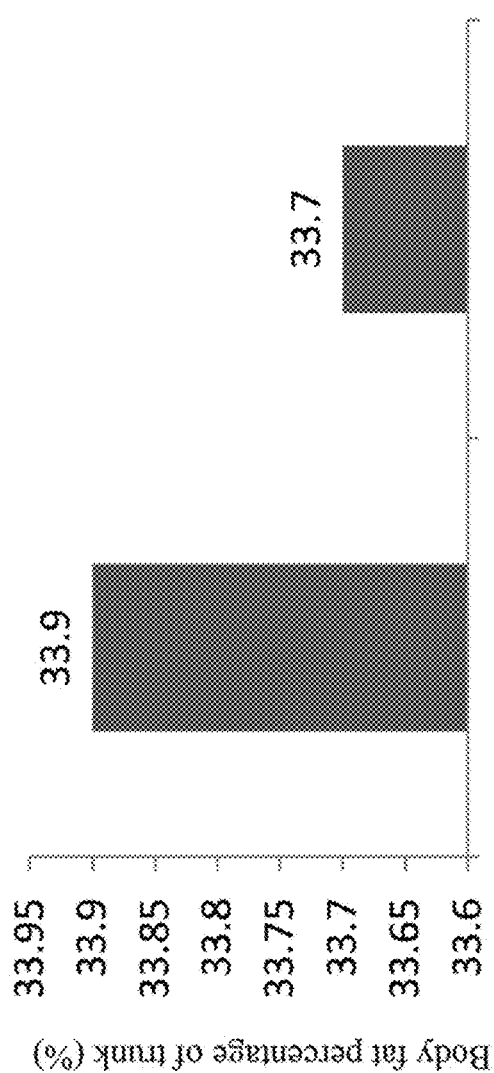
FIG. 12 is a graph showing the results of changes in body fat content of the trunk as evaluated in a human subject experiment.

FIG. 12 is a graph showing the results of changes in body fat content of the trunk as evaluated in a human subject experiment. The initial average trunk body fat content of the 10 subjects was 33.9%, and the final average trunk body fat content of the 10 subjects was 33.7% after taking the early harvested rice prebiotics for four weeks. This means that taking the early harvested rice prebiotics for four weeks can reduce the trunk body fat content by 0.2%.

Herein, the total body fat content of the entire body and the body fat content of the trunk in FIG. 11 and FIG. 12 were measured using a body fat meter (brand: TANITA BC-601FS).

Figure 13:
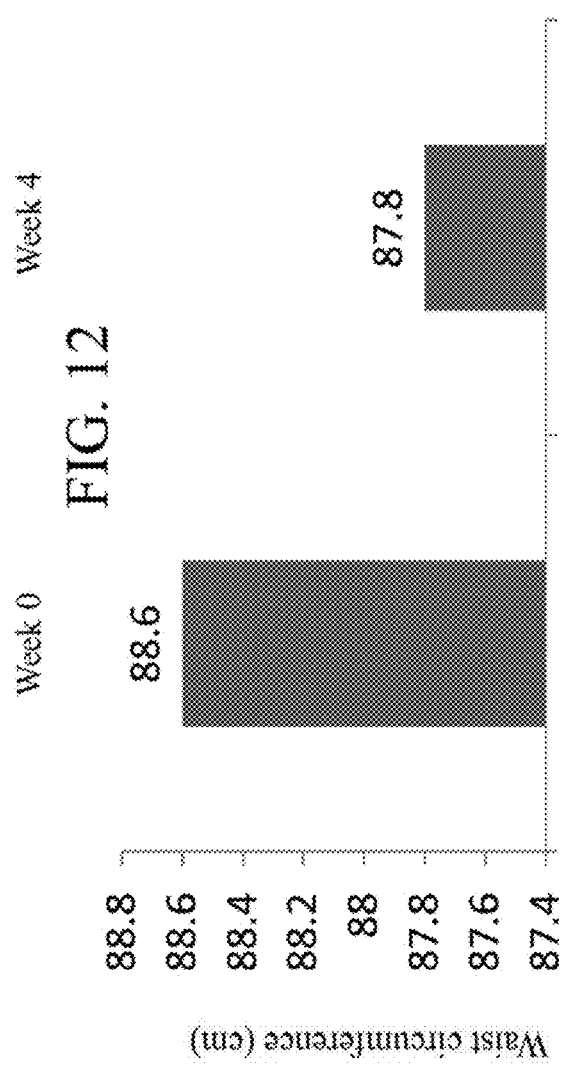
FIG. 13 is a graph showing the results of changes in waist circumference as evaluated in a human subject experiment.

FIG. 13 is a graph showing the results of changes in waist circumference as evaluated in a human subject experiment. The initial average waist circumference of the 10 subjects was 88.6 cm, and the final average waist circumference of the 10 subjects after taking the early harvested rice prebiotics for four weeks was 87.8 cm. This means that taking the early harvested rice prebiotics for four weeks can reduce the waist circumference by 0.8 cm.

Figure 14:
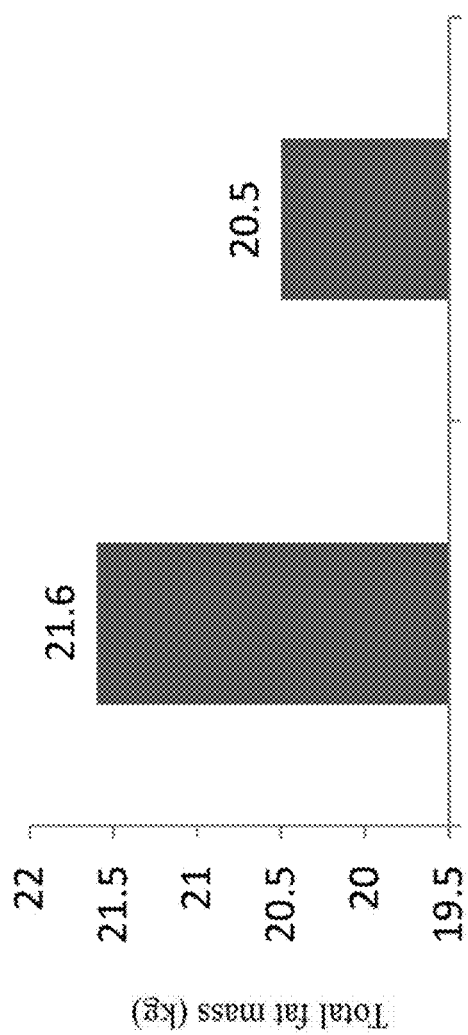
FIG. 14 is a graph showing the results of changes in total fat mass as evaluated in a human subject experiment.

FIG. 14 is a graph showing the results of changes in total fat mass as evaluated in a human subject experiment. The initial average total fat mass of the 10 subjects was 21.6 kg, and the final average total fat mass of the 10 subjects was 20.5 kg after taking the early harvested rice prebiotics for four weeks. This means that taking the early harvested rice prebiotics for four weeks can reduce the total fat mass by 1.1 kg.

Figure 15:
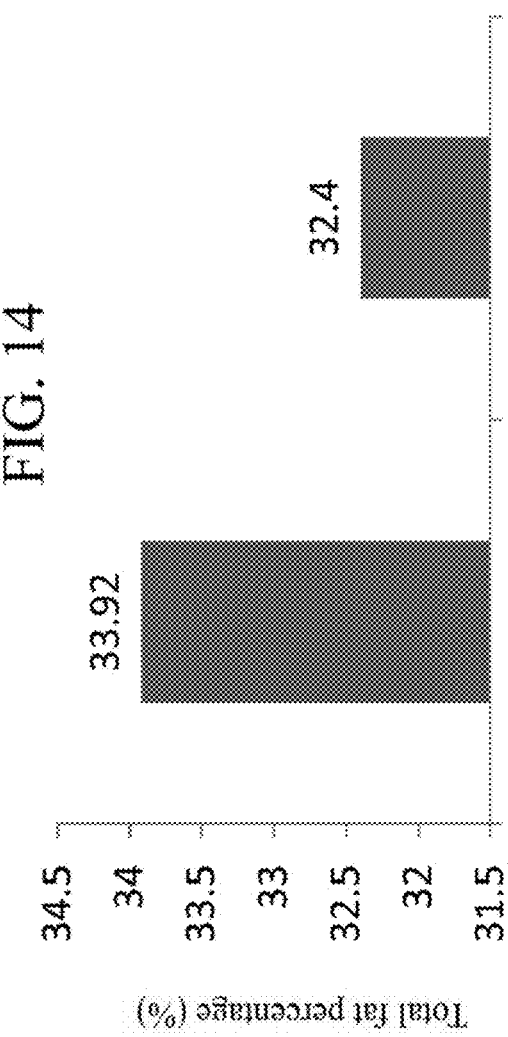
FIG. 15 is a graph showing the results of changes in total fat percentage as evaluated in a human subject experiment.

FIG. 15 is a graph showing the results of changes in total fat percentage as evaluated in a human subject experiment. The initial average total fat percentage of the 10 subjects was 33.92%, and the final average total fat percentage of the 10 subjects after taking the early harvested rice prebiotics for four weeks was 32.4%. This means that the early harvested rice prebiotics harvesting in four weeks can reduce the total fat percentage by 1.52%.

Figure 16:
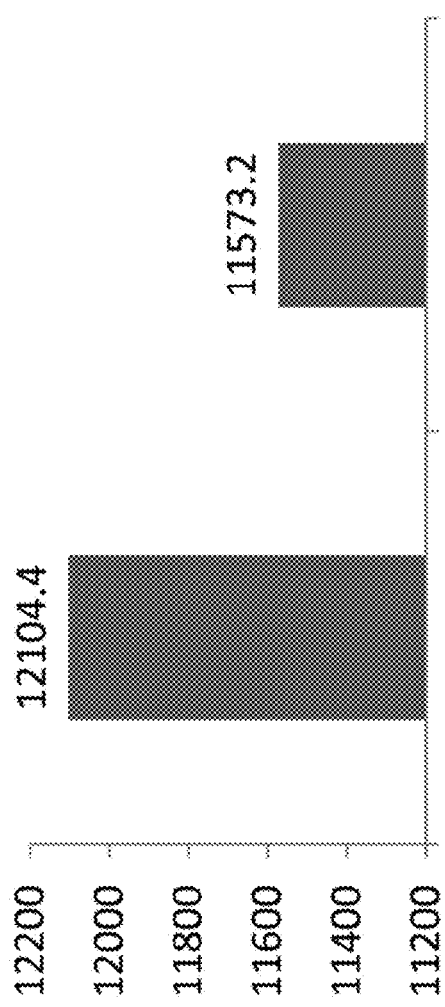
FIG. 16 is a graph showing the results of changes in trunk fat content as evaluated in a human subject experiment.

FIG. 16 is a graph showing the results of changes in trunk fat content as evaluated in a human subject experiment. Herein, the trunk refers to the part of the entire body other than the head and limbs. The initial average total fat mass of the 10 subjects was 12104.4 g, and the final average total fat mass of the 10 subjects after taking the early harvested rice prebiotics for four weeks was 11573.2 grams. This means that taking the early harvested rice prebiotics for four weeks can reduce the total fat mass 531.2 g.

Figure 17:
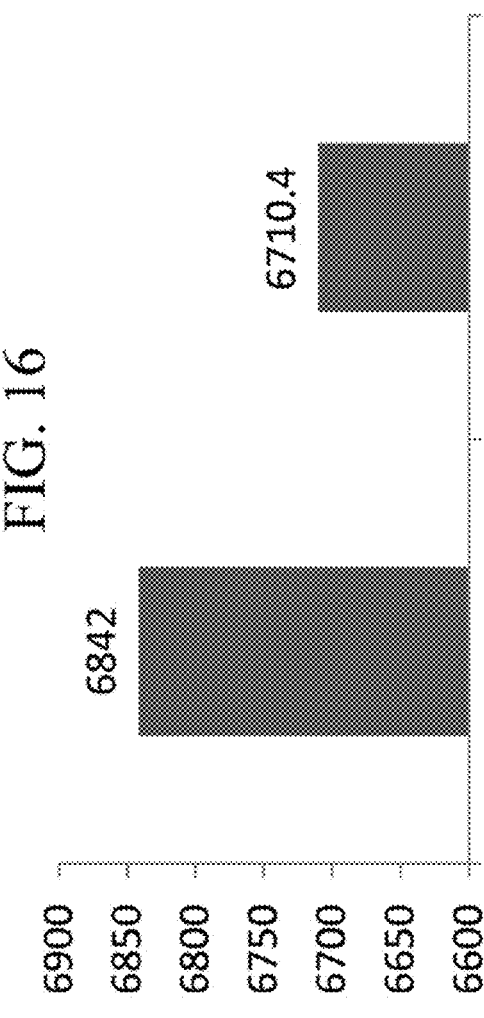
FIG. 17 is a graph showing the results of changes in leg fat mass as evaluated in a human subject experiment.

FIG. 17 is a graph showing the results of changes in leg fat mass as evaluated in a human subject experiment. The initial average total fat mass of the 10 subjects was 6842 g, and the final average total fat mass of the 10 subjects after taking the early harvested rice prebiotics for four weeks was 6710.4 grams. This means that taking the early harvested rice prebiotics for four weeks can reduce the total fat mass to 131.6 grams.

Herein, the total fat mass, total fat percentage, trunk fat content, and leg fat mass in FIG. 14 to FIG. 17 were measured using a dual-energy X-ray absorptiometer (DXA for short, brand: Horizon® DXA System).

Among the 10 subjects mentioned above, 1 was diagnosed with hyperglycemia. This subject had blood tests in week 0, week 2 and week 4. The test items included fasting blood glucose, fasting insulin, and insulin resistance, which were measured by Lezen Reference Lab in Taiwan.

Figure 18:
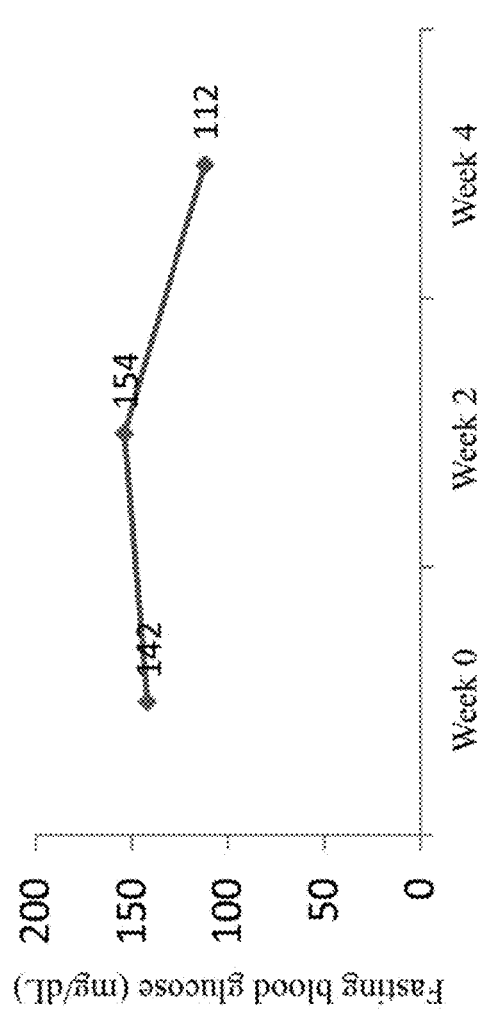
FIG. 18 is a graph showing the results of changes in fasting blood glucose in human subject experiment.

FIG. 18 is a graph showing the results of changes in fasting blood glucose in a human subject experiment. The initial average fasting blood glucose of the subjects was 142 mg/dL, the final average fasting blood glucose of the subjects was 154 mg/dL after taking the early harvested rice prebiotics for two weeks, and the final average fasting blood glucose of the subject after taking the early harvested rice prebiotics for four weeks was 112 mg/dL. Generally speaking, the normal fasting blood glucose range is 74 mg/dL-118 mg/dL. That is to say, taking the early harvested rice prebiotics for four weeks had a significant effect of reducing the fasting blood glucose of patients with hyperglycemia to the normal range.

Figure 19:
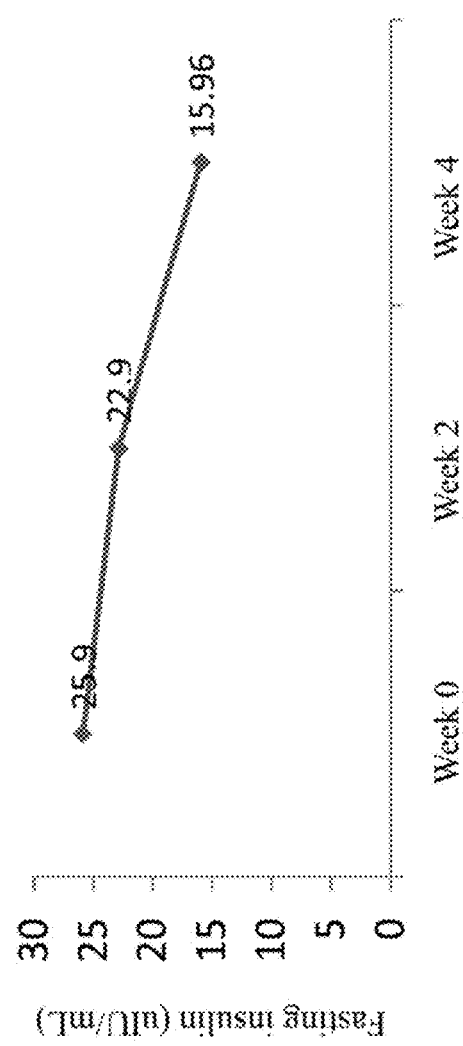
FIG. 19 is a graph showing the results of changes in fasting insulin in a human subject experiment.

FIG. 19 is a graph showing the results of changes in fasting insulin in a human subject experiment. The initial average fasting insulin of the subjects was 25.9 uIU/mL, the final average fasting insulin of the subjects after taking the early harvested rice prebiotics for two weeks was 22.9 uIU/mL, and the final average fasting insulin of the subjects after taking the early harvested rice prebiotics for four weeks was 15.96 uIU/mL. Generally speaking, the normal fasting insulin range is 4 uIU/mL-16 uIU/mL. That is to say, taking the early harvested rice prebiotics for four weeks had a significant effect of reducing the fasting insulin of patients with hyperglycemia to the normal range.

Figure 20:
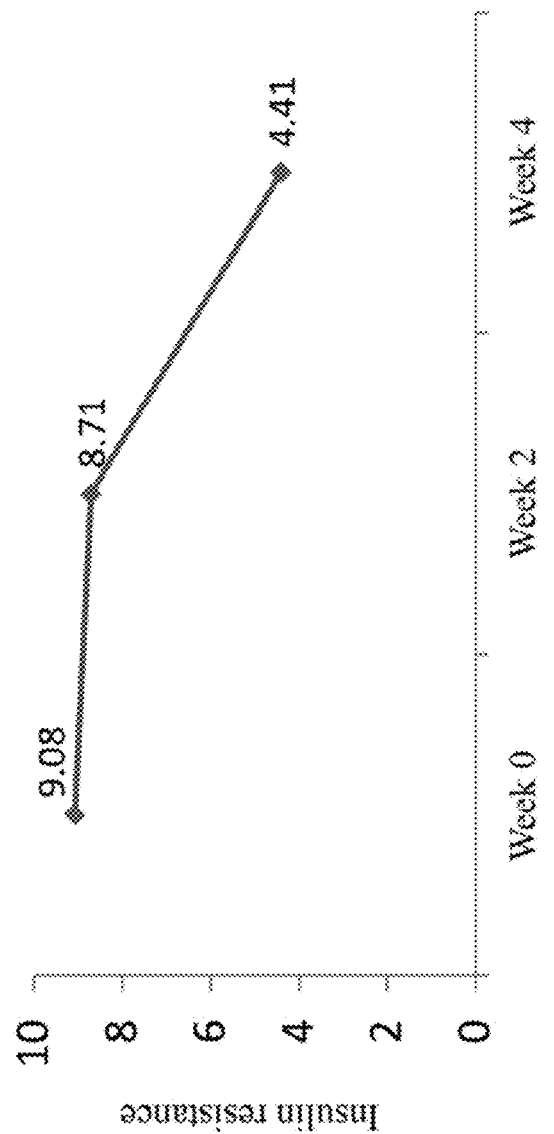

FIG. 20 is a graph showing the results of changes in insulin resistance in a human subject experiment. The initial average insulin resistance (IR) of the subjects was 9.08, the final average insulin resistance of the subjects after taking the early harvested rice prebiotics for two weeks was 8.71, and the final average insulin resistance of the subjects after taking the early harvested rice prebiotics for four weeks was 4.41. Generally speaking, the normal insulin resistance is less than 1 (<1), levers over 1.9 indicates moderate insulin resistance, and levels over 2.9 indicates severe insulin resistance. That is to say, the insulin resistance of the subjects was reduced by 50% or more this time, indicating a significant effect.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A method for slimming and/or promoting probiotics growth, comprising administering to a subject in need thereof a composition comprising an effective dose of early harvested rice prebiotics, wherein the early harvested rice prebiotics comprise peptides as set forth in SEQ 1D NO: 1, SEQ 1D NO: 2, SEQ 1D NO: 3, SEQ ID NO: 4, SEQ ID NO: 5, SEQ ID NO: 6, SEQ ID NO: 7 and SEQ ID NO: 8.

2. The method according to claim 1, wherein the early harvested rice prebiotics are prepared from early harvested rice, and the early harvested rice are rice seeds that are harvested within 15 to 25 days after flowering.

3. The method according to claim 2, wherein the early harvested rice prebiotics are prepared from the early harvested rice by aqueous extraction and hydrolysis with an alkaline protease.

4. The method according to claim 1, wherein the early harvested rice prebiotics are used to increase the content of leptin, adiponectin or glucose transporter type 4 (GLUT4) protein.

5. The method according to claim 1, wherein the early harvested rice prebiotics are used to increase the amounts of probiotics in human intestinal tract of the subject.

6. The method according to claim 5, wherein the probiotics are *Lactobacillus acidophilus, Lactobacillus reuteri, Lactobacillus rhanmosus, Lactobacillus paracasei* or *Rhizopus bifidus*.

7. The method according to claim 1, wherein the early harvested rice prebiotics are used to reduce body fat content in the subject.

8. The method according to claim 1, wherein the early harvested rice prebiotics are used to reduce waist circumference, trunk fat content, or leg fat content of the subject.

9. The method according to claim 1, wherein the early harvested rice prebiotics are used to reduce fasting blood glucose, fasting insulin or insulin resistance.

10. The method according to claim 1, wherein the effective dose of the early harvested rice prebiotic is 500 mg.

* * * * *

SEQUENCE LISTING

```
<160> NUMBER OF SEQ ID NOS: 9

<210> SEQ ID NO 1
<211> LENGTH: 13
<212> TYPE: PRT
<213> ORGANISM: Ozaya sativa

<400> SEQUENCE: 1

Arg Gln Gly Asp Val Ile Ala Leu Pro Ala Gly Val Ala
1               5                   10

<210> SEQ ID NO 2
<211> LENGTH: 7
<212> TYPE: PRT
<213> ORGANISM: Ozaya sativa

<400> SEQUENCE: 2

Ile Leu Ala Gly Asp His Leu
1               5

<210> SEQ ID NO 3
<211> LENGTH: 13
<212> TYPE: PRT
<213> ORGANISM: Ozaya sativa

<400> SEQUENCE: 3

Asn Ser Ile Asp Ser Ser Thr Ile Ala Ser Asn Ile Lys
1               5                   10

<210> SEQ ID NO 4
<211> LENGTH: 17
<212> TYPE: PRT
<213> ORGANISM: Ozaya sativa

<400> SEQUENCE: 4

Val Ser Asp Ser Gln Ile Pro Leu Thr Gly Ala His Ser Ile Ile Gly
1               5                   10                  15

Arg

<210> SEQ ID NO 5
<211> LENGTH: 9
<212> TYPE: PRT
<213> ORGANISM: Ozaya sativa

<400> SEQUENCE: 5
```

```
Ile Ser Pro Ser Ala Pro Val Val Arg
1               5

<210> SEQ ID NO 6
<211> LENGTH: 7
<212> TYPE: PRT
<213> ORGANISM: Ozaya sativa

<400> SEQUENCE: 6

Val Ser Pro Asp Val Gln Phe
1               5

<210> SEQ ID NO 7
<211> LENGTH: 10
<212> TYPE: PRT
<213> ORGANISM: Ozaya sativa

<400> SEQUENCE: 7

Val Arg Ser Leu Pro Asn Tyr Gly Gly Leu
1               5                   10

<210> SEQ ID NO 8
<211> LENGTH: 9
<212> TYPE: PRT
<213> ORGANISM: Ozaya sativa

<400> SEQUENCE: 8

Pro His Tyr Ser Asn Gly Ala Thr Leu
1               5

<210> SEQ ID NO 9
<211> LENGTH: 12
<212> TYPE: PRT
<213> ORGANISM: Ozaya sativa

<400> SEQUENCE: 9

Val Arg Gln Gln Tyr Gly Ile Ala Ala Ser Pro Phe
1               5                   10
```